(12) United States Patent
Magana et al.

(10) Patent No.: US 11,291,434 B2
(45) Date of Patent: Apr. 5, 2022

(54) SYSTEMS, METHODS, AND DEVICES FOR FALLOPIAN TUBE DIAGNOSTICS

(71) Applicant: NVISION MEDICAL CORPORATION, San Bruno, CA (US)

(72) Inventors: Jesus Magana, Redwood City, CA (US); David W. Snow, San Carlos, CA (US); Alan L. Bradley, San Francisco, CA (US); Christina Christman-Skieller, San Bruno, CA (US); Surbhi Sarna, San Bruno, CA (US)

(73) Assignee: NVISION MEDICAL CORPORATION, San Bruno, CA (US)

( * ) Notice: Subject to any disclaimer, the term of this patent is extended or adjusted under 35 U.S.C. 154(b) by 541 days.

(21) Appl. No.: 15/998,507

(22) Filed: Aug. 16, 2018

(65) Prior Publication Data

US 2019/0000429 A1  Jan. 3, 2019

Related U.S. Application Data

(63) Continuation-in-part of application No. 15/053,568, filed on Feb. 25, 2016, now Pat. No. 10,639,016,
(Continued)

(51) Int. Cl.
*A61B 10/02* (2006.01)
*A61M 25/01* (2006.01)
(Continued)

(52) U.S. Cl.
CPC ...... *A61B 10/0291* (2013.01); *A61B 17/3421* (2013.01); *A61B 90/39* (2016.02);
(Continued)

(58) Field of Classification Search
None
See application file for complete search history.

(56) References Cited

U.S. PATENT DOCUMENTS 2,701,559 A * 2/1955 Cooper ................. A61B 10/02
600/569
3,168,092 A   2/1965 Silverman
(Continued)

FOREIGN PATENT DOCUMENTS

AU  2015218548 A1  9/2015
DE     3331813 A1  3/1985
(Continued)

OTHER PUBLICATIONS

International Preliminary Report on Patentability for the International Patent Application No. PCT/US2018/000229, dated Feb. 27, 2020, 7 pages.
(Continued)

*Primary Examiner* — Sean P Dougherty
*Assistant Examiner* — Benjamin S Melhus
(74) *Attorney, Agent, or Firm* — Seager, Tufte & Wickhem LLP.

(57) ABSTRACT

The present disclosure generally relates to devices, systems, and methods for Fallopian tube diagnostics. In some embodiments, a tube may have a distal end, and a balloon may be coupled to the distal end of the tube. The balloon may be disposed in the tube in a first, inverted position and movable to a second, everted position. The balloon may be extendable a distance distal of the tube distal end such that a surface of the balloon is contactable with an inner surface of the Fallopian tube. A push wire may have a distal end coupled to a second end of the balloon. The balloon may be movable from the first inverted position to the second everted position by actuation of the push wire. The surface of the balloon may include a plurality of surface features for
(Continued)

collection of a tissue sample of the inner surface of the Fallopian tube.

20 Claims, 21 Drawing Sheets

Related U.S. Application Data which is a continuation-in-part of application No. 14/764,710, filed as application No. PCT/US2014/014472 on Feb. 3, 2014, now Pat. No. 10,646,209.

(60) Provisional application No. 62/660,512, filed on Apr. 20, 2018, provisional application No. 62/546,791, filed on Aug. 17, 2017, provisional application No. 61/873,753, filed on Sep. 4, 2013, provisional application No. 61/759,783, filed on Feb. 1, 2013.

(51) Int. Cl.

| | | |
|---|---|---|
| *A61B 17/34* | (2006.01) | |
| *A61B 90/00* | (2016.01) | |
| *A61B 17/12* | (2006.01) | |
| *A61M 25/10* | (2013.01) | |
| *A61B 1/00* | (2006.01) | |
| *A61M 25/06* | (2006.01) | |
| *A61M 25/00* | (2006.01) | |
| *A61B 17/42* | (2006.01) | |
| *A61B 17/00* | (2006.01) | |
| *A61B 1/303* | (2006.01) | |

(52) U.S. Cl.
CPC ...... *A61M 25/0113* (2013.01); *A61B 1/00082* (2013.01); *A61B 1/303* (2013.01); *A61B 17/1204* (2013.01); *A61B 17/12099* (2013.01); *A61B 17/12136* (2013.01); *A61B 2010/0208* (2013.01); *A61B 2010/0216* (2013.01); *A61B 2017/00407* (2013.01); *A61B 2017/00557* (2013.01); *A61B 2017/3435* (2013.01); *A61B 2017/4233* (2013.01); *A61B 2090/363* (2016.02); *A61B 2090/392* (2016.02); *A61B 2090/3966* (2016.02); *A61B 2090/3987* (2016.02); *A61M 25/0119* (2013.01); *A61M 25/1002* (2013.01); *A61M 25/10181* (2013.11); *A61M 2025/0004* (2013.01); *A61M 2025/0096* (2013.01); *A61M 2025/0681* (2013.01); *A61M 2025/109* (2013.01); *A61M 2025/1056* (2013.01); *A61M 2025/1065* (2013.01); *A61M 2025/1086* (2013.01); *A61M 2025/1093* (2013.01); *A61M 2210/1425* (2013.01); *A61M 2210/1433* (2013.01)

(56) References Cited

U.S. PATENT DOCUMENTS

| | | | |
|---|---|---|---|
| 3,500,819 A * | 3/1970 | Silverman | A61B 1/00151 600/7 |
| 3,664,328 A | 5/1972 | Moyle, Jr. | |
| 4,324,262 A | 4/1982 | Hall | |
| 4,467,816 A | 8/1984 | Schluter et al. | |
| 4,863,440 A | 9/1989 | Chin | |
| 4,946,440 A | 8/1990 | Hall | |
| 5,163,927 A | 11/1992 | Woker et al. | |
| 5,171,305 A | 12/1992 | Schickling et al. | |
| 5,231,992 A * | 8/1993 | Leon | A61B 10/0045 128/841 |
| 5,364,345 A * | 11/1994 | Lowery | A61M 25/0119 600/116 |
| 5,374,247 A | 12/1994 | Lowery et al. | |
| 5,389,089 A * | 2/1995 | Bauer | A61M 25/0069 600/35 |
| RE35,312 E * | 8/1996 | Christoudias | A61B 17/00234 600/207 |
| 5,630,797 A | 5/1997 | Diedrich et al. | |
| 5,738,109 A | 4/1998 | Parasher | |
| 6,383,805 B1 | 5/2002 | Latimer | |
| 6,475,164 B2 * | 11/2002 | Gombrich | A61B 10/0291 600/569 |
| 6,514,224 B1 * | 2/2003 | Anapliotis | A61B 10/00 206/209 |
| 6,840,946 B2 | 1/2005 | Fogarty et al. | |
| 7,255,687 B2 | 8/2007 | Huang et al. | |
| 8,470,043 B2 | 6/2013 | Schaller et al. | |
| 8,652,067 B2 | 2/2014 | Lonky et al. | |
| 8,992,438 B2 * | 3/2015 | Loktionov | A61B 10/04 600/562 |
| 9,028,401 B1 | 5/2015 | Bacich et al. | |
| 9,161,773 B2 | 10/2015 | Schaller et al. | |
| 9,282,951 B2 | 3/2016 | Lonky et al. | |
| 9,320,502 B2 | 4/2016 | O'Sullivan et al. | |
| 9,339,259 B2 * | 5/2016 | Loktionov | A61B 10/0096 |
| 9,492,570 B2 | 11/2016 | Sirimanne et al. | |
| 9,493,839 B2 | 11/2016 | Speiser et al. | |
| 2003/0208223 A1 | 11/2003 | Kleiner | |
| 2004/0030263 A1 | 2/2004 | Dubrul et al. | |
| 2005/0021069 A1 | 1/2005 | Feuer et al. | |
| 2006/0079924 A1 | 4/2006 | Sanders et al. | |
| 2007/0213753 A1 | 9/2007 | Waller | |
| 2008/0097238 A1 * | 4/2008 | Loktionov | A61B 10/0038 600/562 |
| 2008/0188769 A1 * | 8/2008 | Lu | A61B 10/02 600/569 |
| 2009/0287238 A1 | 11/2009 | Behl et al. | |
| 2012/0259401 A1 | 10/2012 | Gerrans et al. | |
| 2012/0315662 A1 | 12/2012 | Linnemeier | |
| 2013/0253426 A1 * | 9/2013 | Campbell | A61L 29/085 604/103.02 |
| 2013/0267870 A1 | 10/2013 | Lonky | |
| 2013/0338533 A1 | 12/2013 | Olsen | |
| 2014/0128732 A1 | 5/2014 | Roy et al. | |
| 2014/0257098 A1 | 9/2014 | Del Priore | |
| 2015/0057565 A1 | 2/2015 | Mazzoli, Jr. et al. | |
| 2016/0278747 A1 | 9/2016 | Chin et al. | |
| 2017/0354437 A1 | 12/2017 | Bacich | |
| 2018/0014773 A1 | 1/2018 | Barton et al. | |

FOREIGN PATENT DOCUMENTS

| | | |
|---|---|---|
| EP | 0004318 A2 | 10/1979 |
| EP | 0539084 A1 | 4/1993 |
| GB | 1573819 A | 8/1980 |
| JP | S5532576 A | 3/1980 |
| JP | 2013517907 A | 5/2013 |
| WO | 0170297 A2 | 9/2001 |
| WO | 2009142605 A1 | 11/2009 |

OTHER PUBLICATIONS

International Search Report and Written Opinion for application No. PCT/US2018/000229, dated Dec. 4, 2018, 13 pages.
Peng, L et al., "Micro hot embossing of thermoplastic polymers: a review", Journal of Micromechanics and Microengineering, 24:1-24 (2014).
De Gans, B-J., "Polymer-Relief Microstructures by Inkjet Etching", Adv. Mater. 18:910-914 (2006).
Lazare, S. et al.,"Ultraviolet Laser Photoablation of Polymers: A Review and Recent Results" Laser Chemistry, 10(1):25-40 (1989).
Puliyalil, H. et al., "Selective Plasma Etching of Polymeric Substrates for Advanced Applications", Nanomaterials 6(108):1-24 (2016).
Nordqvist, C., "Flourescent Dye Lights Up Cancer Cells Making Surgery More Effective", MedicalNewsToday [online], Sep. 2011 [retrieved on Mar. 2, 2019]. Retrieved from Internet URL: https://www.medicalnewstoday.com/articles/234614.php, 4 pages.
Trivedi P., "Female Infertility Surgery: Hysteroscopic Cannulation for Proximal Tubal Block." In The Infertility Manual, Rao KA,

(56) References Cited

OTHER PUBLICATIONS

Brinsden PR, Sathananthan AH, editors, (Kent, United Kingdom: Anshan Ltd.), pp. 213-214 (2005).

* cited by examiner

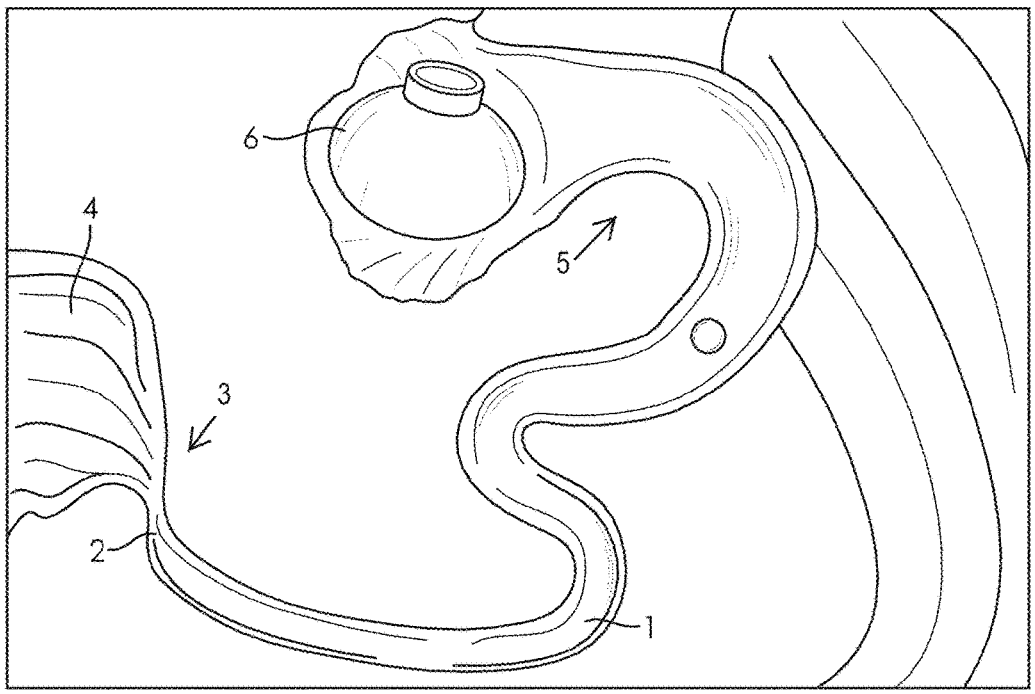
FIG.1
PRIOR ART
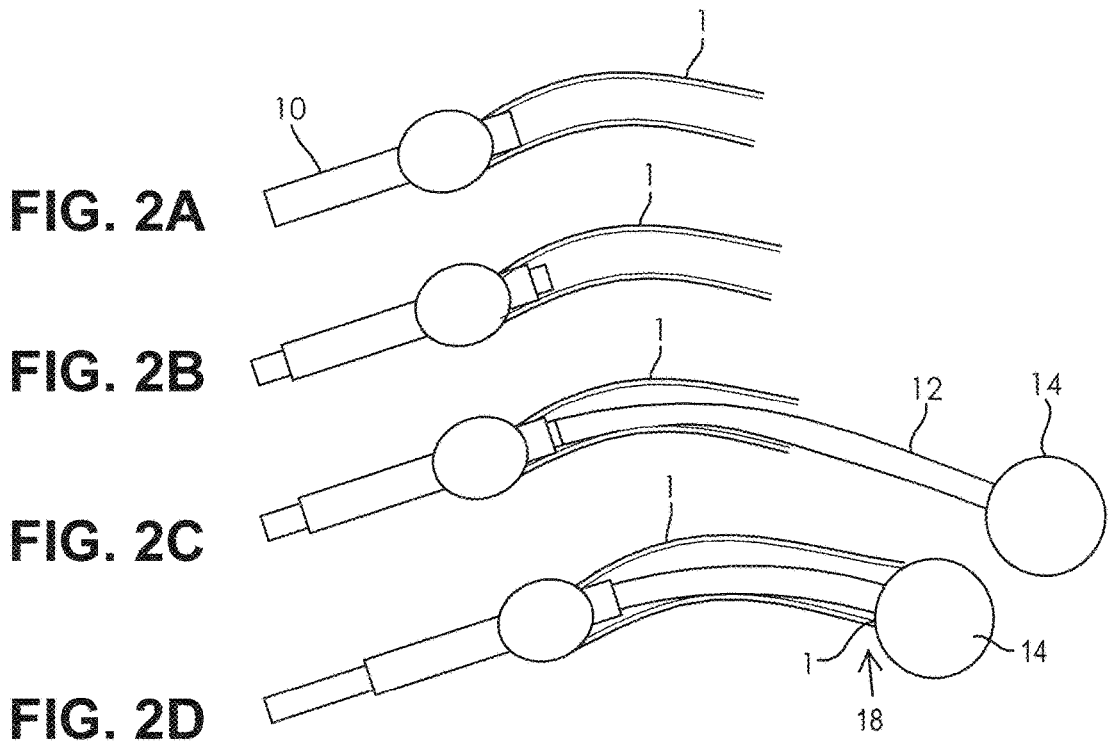
FIG. 2A
FIG. 2B
FIG. 2C
FIG. 2D

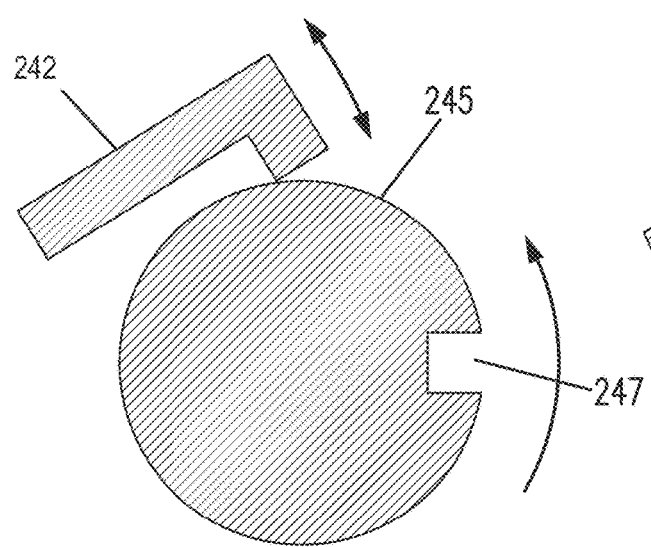 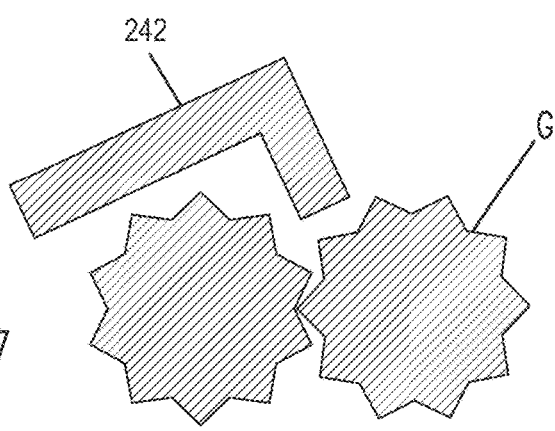
FIG. 26D
FIG. 26E

SYSTEMS, METHODS, AND DEVICES FOR FALLOPIAN TUBE DIAGNOSTICS

CROSS-REFERENCE TO RELATED APPLICATIONS

This application is a continuation in part of, and claims the benefit of priority to, U.S. patent application Ser. No. 15/053,568, filed Feb. 25, 2016, entitled "Methods and Devices for Fallopian Tube Diagnostics," which is a continuation-in-part of U.S. patent application Ser. No. 14/764,710, filed on Jul. 30, 2015, entitled "Methods and Devices for Fallopian Tube Diagnostics," which is a national stage application of International Patent Application Serial No. PCT/US2014/014472, filed Feb. 3, 2014, entitled "Methods and Devices for Fallopian Tube Diagnostics," which claims priority to U.S. Provisional Patent Application Ser. No. 61/873,753, filed Sep. 4, 2013, entitled "Everting Catheter for Fallopian Tube Diagnostics," and U.S. Provisional Patent Application Ser. No. 61/759,783, filed Feb. 1, 2013, entitled "Methods and Devices for Fallopian Tube Diagnostics," the entire disclosures of which applications are expressly incorporated by reference herein.

This application is a nonprovisional application of, and claims the benefit of priority to, U.S. Provisional Application Ser. No. 62/546,791, filed Aug. 17, 2017, entitled "Devices for Fallopian Tube Diagnostics," and U.S. Provisional Application Ser. No. 62/660,512, filed Apr. 20, 2018, entitled "Methods and Devices for Fallopian Tube Diagnostics," the entire disclosures of which applications are expressly incorporated by reference herein.

FIELD

The present disclosure generally relates to Fallopian tube diagnostics, and in particular to systems, devices, and methods that accommodate the anatomical difficulties associated with navigation of body lumens, including the Fallopian tube, for tissue sample collection.

BACKGROUND

Ovarian cancer is a significant disease in women, in which 1 out of 72 women in the United States may be diagnosed with this illness during her lifetime. In 2012, over 22,000 women in the United States were diagnosed with ovarian cancer. Early detection of ovarian cancer may be difficult due to a lack of effective screening tests, such that ovarian cancer may not be diagnosed until the disease has reached advanced stages, limiting treatment options.

Screening for ovarian cancer may typically include a surgical procedure for obtaining cell samples for diagnosis. For example, because the ovaries are intra-abdominal, laparoscopic or open surgery (laparotomy) may be performed to access the ovaries. Any surgical procedure increases a risk to the patient, including but not limited to experiencing an adverse reaction, and/or requiring significant recovery time. Additionally, an ovary biopsy may expose the patient to additional risk of potentially spreading diseased (e.g., cancerous) cells.

Thus, there exists a need for devices and processes to allow samples to be obtained from a Fallopian tube for evaluation of ovarian cancer in a less invasive and controlled fashion and, particularly without the need for a skin incision. There further exists a need for securing a sample of representative cells from the Fallopian tube with a catheter to screen for early stage cancers.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a device for Fallopian tube diagnostics may include a tube having a distal end and a balloon having a first end coupled to the distal end of the tube. The balloon may be disposed in the tube in a first, inverted position, may be movable to a second, everted position, and may be extendable a distance distal of the tube distal end such that a surface of the balloon is contactable with an inner surface of the Fallopian tube. A push wire may have a distal end coupled to a second end of the balloon. The balloon may be movable from the first inverted position to the second everted position by actuation of the push wire. A surface of the balloon may include a plurality of surface features for collection, retention, or both, of a tissue sample of the inner surface of the Fallopian tube.

In various of the foregoing and other embodiments of the present disclosure, the surface features may include a plurality of wrinkles formed in the surface of the balloon, and may have at least one of plurality of edges, micro-ridges, or overlapping material, or combinations thereof. A plurality of wrinkles may be formable in the balloon surface. A plurality of wrinkles in the balloon surface may be formed in the balloon surface, and may be configured to retain at least a portion of the tissue sample after contacting the inner surface of the Fallopian tube. The surface features may be etched in the surface of the balloon. A portion of the surface of the balloon may be embossed to form a plurality of peaks and valleys. The plurality of surface features may improve adhesion of the tissue sample to the balloon surface compared to the balloon surface without the surface features. The balloon may be inflatable for moving the balloon from the first inverted position to the second everted position. A filament may be attached to the push wire, the filament may be disposed within the balloon in the first inverted position, and the filament may be extendable from the balloon in the second everted position.

According to an exemplary embodiment of the present disclosure, a system for collecting a tissue sample in a body lumen may include a tube having a distal end and a balloon having a first end coupled to the distal end of the tube and a second end coupled to a distal end of a push wire. The balloon may be positionable in a first, inverted state. The push wire may be configured to advance to evert the balloon to a second, everted state, such that the balloon extends out of the distal end of the tube. A surface of the balloon may be configured in the second, everted state, to contact an inner surface of the body lumen for transference of the tissue sample to the balloon surface. The balloon surface may include a plurality of surface features for collection, retention, or both, of the tissue sample.

In various of the foregoing and other embodiments of the present disclosure, the surface features may include a plurality of wrinkles formed in the surface of the balloon, having at least one of a plurality of edges, micro-ridges, or overlapping material, or combinations thereof. A plurality of wrinkles may be formable in the balloon surface. A plurality of wrinkles in the balloon surface may be configured to retain at least a portion of the tissue sample after contacting the inner surface of the body lumen. The surface features may be etched in the surface of the balloon. The plurality of surface features may improve adhesion of the tissue sample to the balloon surface compared to the balloon surface without the surface features.

According to an exemplary embodiment of the present disclosure, a method for collecting a tissue sample in a body lumen may include providing a tube having a distal end and a balloon having a first end coupled to the distal end of the tube and a second end coupled to a distal end of a push wire. The balloon may be positioned in a first, inverted state. The push wire may be advanced to evert the balloon to a second, everted state, such that the balloon extends out of the distal end of the tube. A balloon surface may contact in the second, everted state, an inner surface of the body lumen. The balloon surface may include a plurality of surface features for collection, retention, or both, of the tissue sample.

In various of the foregoing and other embodiments of the present disclosure, the surface features may include a plurality of wrinkles formed in the surface of the balloon, and may have at least one of a plurality of edges, micro-ridges, or overlapping material, or combinations thereof. A plurality of wrinkles may be formable in the balloon surface. A plurality of wrinkles in the balloon surface may be configured to retain at least a portion of the tissue sample after contacting the inner surface of the body lumen. The plurality of surface features may improve adhesion of the tissue sample to the balloon surface compared to the balloon surface without the surface features.

According to an exemplary embodiment of the present disclosure, a device for Fallopian tube diagnostics may include a tube having a distal end, and a balloon having a first end coupled to the distal end of the tube. The balloon may be disposed in the tube in a first, inverted position, may be movable to a second, everted position, and may be extendable a distance distal of the tube. An extending portion may have a proximal end coupled to a second end of the balloon. The extending portion may be disposed within the balloon in the first inverted position, and may be extendable from the second end of the balloon in the second everted position.

In various of the foregoing and other embodiments of the present disclosure, the extending portion may be any of a filament, suture, or string, or combinations thereof. At least a portion of the filament, suture, or string, or combinations thereof, may be braided. The extending portion may be formed of one or more filaments having a color. The colors of the one or more filaments of the extending portion may provide for a contrasting visualization. The extending portion may include one or more knots or indicia for one or both of visual and tactile feedback. The extending portion may be a braided filament configured to collect and retain a tissue sample in response to extending from the balloon in the second everted position. A push wire may have a distal end coupled to the second end of the balloon and the proximal end of the extending portion. The balloon and the extending portion may be movable from the first inverted position to the second everted position by actuation of the push wire.

According to an exemplary embodiment of the present disclosure, a system for collecting a tissue sample in a body lumen may include a tube having a distal end, and a balloon may have a first end coupled to the distal end of the tube and a second end. An extending portion may be attached to the second end of the balloon. The balloon and the extending portion may be positionable in a first, inverted state. The balloon and the extending portion may be configured to advance to a second, everted state, such that the balloon and the extending portion may extend out of the distal end of the tube. The extending portion may be disposed within the balloon in the first inverted position, and may be extendable from the balloon in the second everted position into the body lumen.

In various of the foregoing and other embodiments of the present disclosure, the extending portion may be any of a filament, suture, or string, or combinations thereof. At least a portion of the filament, suture, or string, or combinations thereof, may be braided. The extending portion may be formed of one or more filaments having a color. The colors of the one or more filaments of the extending portion may provide for a contrasting visualization. The extending portion may include one or more knots or indicia for one or both of visual and tactile feedback. The extending portion may be a braided filament configured to collect and retain a tissue sample in response to extending from the balloon in the second everted position into the body lumen. A push wire may have a distal end coupled to the second end of the balloon and the proximal end of the extending portion. The balloon and the extending portion may be movable from the first inverted position to the second everted position by actuation of the push wire.

According to an exemplary embodiment of the present disclosure, a method for collecting a tissue sample in a body lumen may include providing a tube having a distal end, and a balloon having a first end coupled to the distal end of the tube and a second end. An extending portion may be attached to the second end of the balloon. The balloon and the extending portion being may be positioned in a first, inverted state. The balloon may be advanced to a second, everted state, such that the balloon and the extending portion may extend out of the distal end of the tube. The extending portion may be disposed within the balloon in the first inverted position, and may be extendable from the balloon in the second everted position into the body lumen.

In various of the foregoing and other embodiments of the present disclosure, the tissue sample may be collected by the extending portion extendable from the balloon in the second everted position into the body lumen. The extending portion may be any of a braided filament, braided suture, or braided string, or combinations thereof. The extending portion may be formed of one or more filaments having a color. The colors of the one or more filaments of the extending portion may provide for a contrasting visualization. The extending portion may be a braided filament and may be configured to collect and retain a tissue sample in response to extending from the balloon in the second everted position into the body lumen. A push wire may have a distal end coupled to the second end of the balloon and the proximal end of the extending portion, and may be actuated to move the balloon and the extending portion from the first inverted position to the second everted position.

According to exemplary embodiments of the present disclosure, devices, systems, and methods for Fallopian tube diagnostics may include a tube having a distal end and a proximal end, and a sheath disposed coaxial to the tube. A balloon may have a first end coupled to the distal end of the tube and a second end, and the sheath may extend over the balloon. The sheath may provide column strength to the balloon as the balloon moves from a first, inverted position to a second, everted position, into the Fallopian tube. The sheath may minimize balloon collapse as the balloon is everted into the Fallopian tube. The sheath may protect the everted balloon or an extended portion, or both after cell collection during removal from the patient. A sheath knob may connect the sheath to the tube. The sheath knob may be configured to lock the sheath to the tube to minimize relative movement. The sheath knob may be configured to unlock the sheath from the tube for adjusting the sheath relative to the balloon and the tube.

According to exemplary embodiments of the present disclosure, devices, systems, and methods for Fallopian tube diagnostics may include one or more markers for visualization. A first marker may be disposed on a tube, and may indicate a position of the tube relative to the sheath, or sheath knob. The first marker may indicate positioning of the sheath relative to the tube as a preparation step to cover at least a portion of a balloon in a second, everted position. The first marker may indicate positioning of the sheath relative to the tube for initial advancement of the balloon into the Fallopian tube. In response to at least a portion of the balloon in the second, everted position, the sheath may be moved in a proximal direction to expose at least the portion of the balloon. A second marker may be disposed on the tube, and may indicate a position of the tube relative to the sheath or sheath knob. The second marker may indicate positioning of the sheath relative to the tube as a retraction marker, for visualization that the sheath covers the everted balloon and/or extending portion after cell collection to protect the collected cells. The second marker may be disposed at a proximal portion of the tube. A third marker may be disposed on a tube, and may be at a distal end of the tube relative to a connection point of the balloon and the tube. The third marker may visually indicate an end of the tube, to confirm a balloon and/or extending portion extension or positioning in the Fallopian tube. The one or more markers may be formed as a score line, a coating substance, or band of material, or combinations thereof. The one or more markers may improve or standardize balloon positioning and extension into the Fallopian tube. A seal may be disposed around a push wire and positioned relative to a pressurized chamber 116. The push wire may be movable relative to the seal for advancing through the tube to actuate the balloon between a first, inverted position and a second, everted position. In response to a leak formation between the push wire and the conical seal, a seal may be adjustable to maintain pressure for moving the balloon between a first inverted position and a second everted position.

According to exemplary embodiments of the present disclosure, devices, systems, and methods for Fallopian tube diagnostics may include that at least a portion of the sheath may be translucent, transparent, or otherwise see-through. At least a portion of the tube may be translucent, transparent, or otherwise see-through. At least a portion of the balloon may be translucent, transparent, or otherwise see-through. The tube may include a transparent portion and an opaque portion. The opaque portion may be disposed at a proximal end of the tube. The transparent portion of the tube may be more flexible than the opaque portion of the tube. The transparent portion of the tube may extend along the length and along an inner diameter of the opaque portion of the tube. An extending portion may be connected to the balloon and may be disposed within the balloon in the first, inverted position, and may extend from the balloon in the second, everted position. The extending portion may be visible through the balloon, the tube, and the sheath when in the first, inverted position. The balloon may be inflatable by an opaque, or otherwise visible or detectable fluid for visibility to move from the first, inverted position, to the second, everted position.

According to exemplary embodiments of the present disclosure, devices, systems, and methods for Fallopian tube diagnostics may include a handle including a gear mechanism for actuation of the push wire. The gear mechanism may include a plurality of gears and operable by a drive wheel. The gear mechanism may include a step-down ratio for additional control of balloon movement. The drive wheel and gear mechanism may provide for uniform movement of the balloon during movement between the first inverted position and the second everted position. In response to extending the push wire to its proximal end, the handle may include a limit mechanism for providing audible or tactile feedback to a user. A pawl may be engageable with one or more gears, for stopping gear rotation. A pawl may be biased toward a gear rack by a spring. The pawl may engage with and slide over teeth of the gear rack for providing audible or tactile feedback the user. The teeth may have a steeper slope on a first side and a more moderate slope on a second side.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1 illustrates a cross-sectional view of a Fallopian tube with the uterotubal junction (UTJ) that connects the uterus to the ovaries;

FIGS. 2A-2D illustrate exemplary embodiments of a sequential insertion of an insertion catheter into a Fallopian tube in accordance with the present disclosure;

FIG. 26D illustrates a side view of an exemplary embodiment of a drop key-click of the linear rack ratcheting assembly of FIG. 26C in accordance with the present disclosure;

FIG. 26E illustrates a side view of an exemplary embodiment of a gear jam in accordance with the present disclosure;

DETAILED DESCRIPTION

Figure 3:
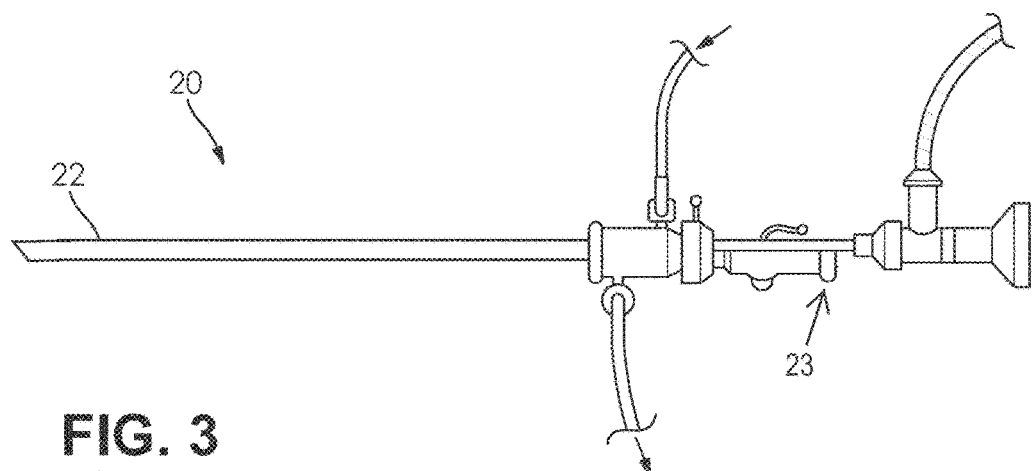
FIG. 3 illustrates a schematic of a hysteroscope for deploying an exemplary embodiment of a catheter in accordance with the present disclosure.

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As described above, a challenge in effectively testing for early stage cancers (e.g., ovarian cancer) in women may include obtaining biopsy samples without undergoing a surgical procedure. Anatomically, the ovaries are in close proximity to the fimbria at the region of the distal opening or os of the Fallopian tube. Eggs released by the ovary may be gathered by the fimbria and transported through the Fallopian tube to the uterus. With ovarian cancer, cells may be deposited in the Fallopian tube, which may eventually migrate into the uterus. Cell samples obtained from the uterus may detect ovarian malignancy; however, the incidence of migration of ovarian cancer cells into the uterus may be too low to render uterine sampling a reliable diagnostic test for ovarian malignancy.

A higher number of cancer cells may migrate to or originate in the Fallopian tube, which may be concentrated in the distal portion of the tube, near the distal os. The ability to test cells in the Fallopian tube for malignancy may be of clinical value for the early detection and treatment of such cancers. It is understood that early detection screening may be performed that detects migrating cancerous cells.

The Fallopian tube is extremely fragile and may be prone to perforation in a medical procedure. As such, safe introduction of a diagnostic device into the Fallopian tube may be difficult with known devices. Referring now to FIG. 1, a Fallopian tube 1 of a patient may extend from a proximal os 3 to a uterus, connecting at a uterotubal junction (UTJ) 2, to a distal os 5 and connecting to ovaries 6. A perforation may occur at the UTJ 2, which is a constriction occurring distal to the proximal os 3 (e.g., opening) of the Fallopian tube. For example, in some patients the UTJ 2 may be approximately 1 cm distal of the proximal os 3. In some patients, the body lumen size at this constriction may be as small as approximately 0.3 mm or 0.5 mm, while the body lumen size of the Fallopian tube adjacent to the UTJ may be approximately 1 mm.

According to exemplary embodiments, systems and methods of the present disclosure may engage an interior wall of a Fallopian tube and may remove cells therefrom for diagnostic purposes. Devices and processes may be provided for collecting such cells in a less invasive procedure that in some embodiments occur without cutaneous incision. Although the description refers to sample collection and diagnostics of Fallopian tubes, it is understood that systems and methods of sample collection and diagnostics may be applicable to any other body lumens, tubes, and ducts, including but not limited to a bile duct, hepatic duct, cystic duct, pancreatic duct, lymphatic vessels, and circulatory vessels in accordance with the present disclosure.

Embodiments of an exemplary catheter for Fallopian tube diagnostics may be provided for the performance of less invasive procedures including any of the following: (1) access to the proximal os of the Fallopian tube via an intrauterine approach; (2) advancement of an introducer catheter to cannulate and form a fluid tight seal with the proximal os; (3) use of a second catheter inside the introducer catheter to track the length of the Fallopian tube out into the abdominal cavity; (4) inflation of a balloon at the end of the second catheter with retraction of the second catheter until the balloon seals the distal os of the Fallopian tube (retraction of the second catheter may result in contact with the intraluminal surface of the Fallopian tube to dislodge cells for improved sampling); and/or (5) irrigation of the Fallopian tube and recovery of the irrigation fluid for cytology or cell analysis.

Exemplary embodiments of a catheter for Fallopian tube diagnostics for minimally invasive procedures may include any of the following: (1) access to the proximal os of the Fallopian tube via an intrauterine approach; (2) advance of an introducer catheter to cannulate the proximal os; (3) use of a second catheter inside the introducer catheter to track inside the Fallopian tube. An inflated balloon at the end of the second catheter may be advanced across the proximal portion of the Fallopian tube and may be everted further into the Fallopian tube; (4) the balloon may contact the intraluminal surface of the Fallopian tube and may dislodge cells for sampling; and/or (5) the balloon may be removed and inserted into a vial for cell collection and subsequent processing.

Embodiments of an exemplary catheter may be configured for insertion into the Fallopian tube (see FIG. 1). The Fallopian tube has a curvature (e.g., having a tortuous pathway), and the soft tissue of the tube may be collapsible, thereby resulting in multiple constrictions as passage is attempted. As described above, this may be particularly true at the uterotubal junction (UTJ), which may be muscular and therefore more prone to perforation by insertion of medical instruments. In some patients, the UTJ may also present a downward bend with a lumen size at the constriction that may be as small as approximately 0.3 mm or 0.5 mm, while the body lumen size of the Fallopian tube adjacent to the UTJ may be approximately 1 mm.

In at least one embodiment of the present disclosure, an elongated balloon that is initially inverted into a catheter lumen may be deployable. The balloon may partially evert to enter a proximal end of the Fallopian tube, e.g., the UTJ, thereby cannulating the proximal os. The balloon may evert upon pressurization of the balloon from inside the catheter so that an unrolling mechanism of the eversion creates a path through the Fallopian tube regardless of tortuosity or constriction in the Fallopian tube. In some embodiments, the balloon may evert by a push wire advancement, which may be in concert with pressurization. A great majority of the length of the balloon may be substantially inelastic, such that the balloon does not substantially expand and dilate the Fallopian tube as it everts. Balloon expansion may burst or otherwise damage or injure the Fallopian tube. However, exemplary embodiments may also incorporate an elastic distal balloon end expandable to seal the distal os upon retraction of the distal balloon. In embodiments, the device may have a balloon having a sufficient rigidity to cannulate the Fallopian tube and sufficient flexibility for navigation through the tortuous path of the Fallopian tube to minimize potential damage or injury. In some embodiments, the device may include support elements for cannulating the Fallopian tube so that the balloon may not collapse at the proximal os.

Exemplary embodiments of systems and methods of the present disclosure may include positioning, and deployment of, a distal end of a catheter. In some embodiments, a catheter distal end may be deliverable to a proximal end of the Fallopian tube by a hysteroscope. In some embodiments, the hysteroscope may be an exemplary hysteroscope (e.g., FIG. 3). Regardless of the mode of deployment, a retracted portion of a catheter may be extendable to contact the interior wall of the Fallopian tube. It has been surprisingly found that the act of extending a portion of the catheter may remove a sufficient sampling of cells and/or tissue from the Fallopian tube wall to perform histological and/or cytological evaluation. For example, at least a portion of a length of the balloon may contact the Fallopian tube for sample collection. In some embodiments, a majority of the length of the balloon may be substantially inelastic such that the balloon does not substantially expand and dilate the body lumen (e.g., Fallopian tube) as it everts. In some embodiments, the balloon may be sized such that the body lumen does not expand or dilate as the balloon everts. As described above, balloon expansion may burst or injure the subject's body lumen. According to some embodiments and as discussed above with regard to the exemplary balloon catheter, the balloon may be extendable by eversion from a catheter only longitudinally into the body lumen such that the balloon does not substantially expand and dilate the lumen as the balloon everts or is extended into the body lumen (e.g., the Fallopian tube). In some embodiments, the balloon may be extendable longitudinally into the body lumen, where a diameter of an inflated balloon may be up to approximately 10-15% greater than a diameter of a Fallopian tube. Radial expansion of the balloon may be limited or controlled by the majority of the length of the balloon being substantially inelastic. It is appreciated that portions of a balloon that are not intended to be inserted within a lumen structure can be elastomeric and therefore may be expandable in diameter and compliant rather than substantially inelastic. Such a hybrid balloon may be well-suited in embodiments when a seal is desired with the UTJ. Exemplary of situations when a seal is desired may include irrigation of the lumen, filling the lumen with an imaging contrast, diagnosing obstructions, and/or topical contact with a therapeutic agent, such as a chemotherapeutic or an antibiotic.

It has also been surprisingly found that withdrawal of an extended portion of a balloon may remove still more cells. In some embodiments, the extended portion may be retracted prior to catheter removal so as to preclude dispersal of dislodged Fallopian tube cells to surrounding tissue. In some embodiments, a slidable sheath may be deployable to protect the collected sample. Upon catheter removal the extended portion may deposit at least a portion of the collected sample (e.g., luminal cells) via contact with a microscope slide or other diagnostic substrate, for testing for abnormal cells (e.g., cancerous cells). In some embodiments, a dye may be releasable in the Fallopian tube for identifying abnormal and potentially cancerous cells.

Referring now to FIGS. 2A-2D, an inverted inelastic sleeve 12 and an attached distal elastic balloon 14 may be insertable through an introduction catheter 10 that may reside in the working channel 22 of an operative hysteroscope 20 (FIG. 3), and used to cannulate the proximal os of the Fallopian tube 1, as shown in FIG. 2A. At FIG. 2B, the balloon may be inflated to evert the sleeve 12 the length of the Fallopian tube 1 and distend the distal elastic balloon 14. At FIG. 2C, the balloon may be retracted proximally at least partially to seal the distal os 18 of the Fallopian tube 1, after full advancement of the inverted elastic sleeve 12 and inflation of the elastic balloon 14. FIG. 2D illustrates the introduction of saline for irrigation along the length of the Fallopian tube 1 between the introducer catheter 10 and the everted sleeve 12. Retraction of the inflated elastic balloon 14 seals the opening of the distal os. Subsequent collection of the irrigation fluid obtains cell samples from substantially the entire length of the Fallopian tube 1 for cell analysis in the detection of ovarian cancer or other medical conditions. In an embodiment, a dye may be present in the irrigation fluid that is introduced in the Fallopian tube for identifying and/or differentiating abnormal and potentially cancerous cells. An illustrative example of a dye may include a fluorescent imaging agent attached to a modified type of folic acid, which may act as a homing device searching for ovarian cancer cells to attach onto. In some embodiments, a multispectral fluorescent camera may illuminate the detected cells, visually identifying their location, e.g., by a monitor. For ovarian cancer cells to grow and divide, the cells need large amounts of the vitamin (folic acid). Special receptors on the surface of the cancer cells seize the vitamin, and whatever is attached to it, and pull it inside.

Figure 4:
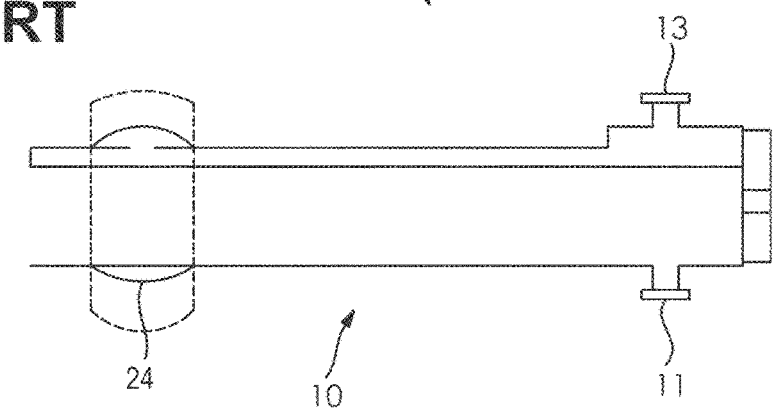
FIG. 4 illustrates an exemplary embodiment of a proximal introducer catheter in accordance with the present disclosure.

The catheter 10 described above, and in greater detail below may be introduced into the uterus of a patient using an operating hysteroscope 20, an example of which is shown in FIG. 3. An operating hysteroscope 20 may include one or more working channels. One channel may provide irrigation to distend the uterus and allow endoscopic visualization, and one or more additional working channels 22 may allow instruments and/or catheters to be advanced distally of the hysteroscope. A proximal introducer catheter 10 (see, e.g., FIG. 2A and FIG. 4) may be advanceable through a working channel of the operating hysteroscope 20, and may be used to cannulate the proximal os of a Fallopian tube. A balloon 24 on the proximal introducer catheter 10 may be inflated to occlude the proximal os (e.g., FIG. 4), and the everting sleeve catheter may be advanceable through the proximal introducer catheter 10 into the proximal portion of the Fallopian tube. The sleeve/balloon element 14 may be fully everted, and the inflated balloon tip may be pulled back to seal the distal os. Irrigation may be introduced via a port 11, and aspirated via the irrigation port 11 on the proximal introducer catheter 10, to collect the sample. Irrigation may also be introduced through both the everting sleeve catheter and the proximal introducer catheter, followed by aspiration through one or both ports (11, 13) of the proximal introducer catheter.

Figure 5A:
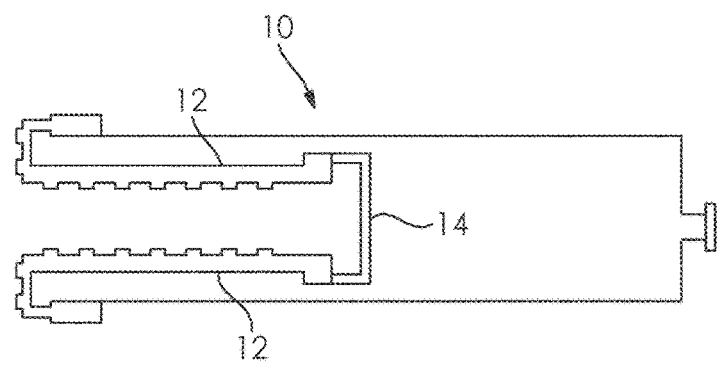
FIG. 5A illustrates a cross-sectional view of an exemplary embodiment of an everting sleeve with a distal elastic balloon tip in a deflated state in accordance with the present disclosure.
Figure 5B:
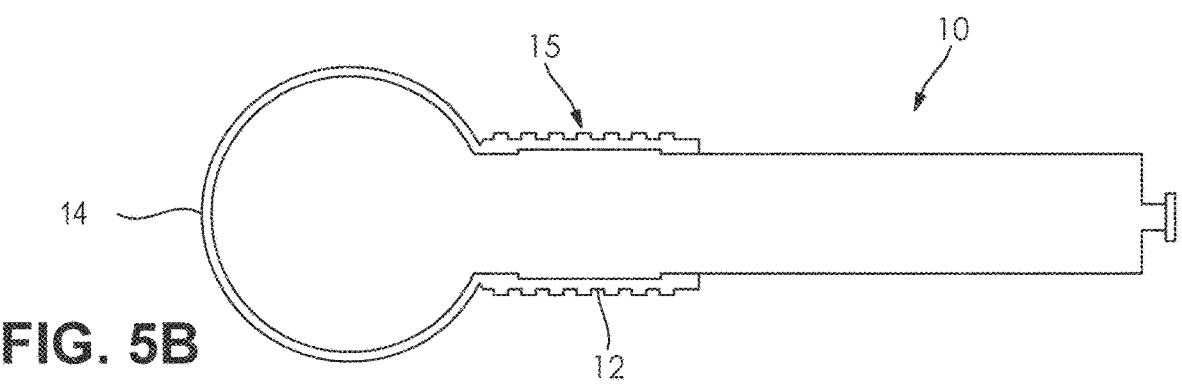
FIG. 5B illustrates a cross-sectional view of the everting sleeve with a distal elastic balloon tip of FIG. 5A in an inflated state in accordance with the present disclosure.

In embodiments of the catheter 10, the sleeve 12 of the everting sleeve catheter may be a flexible, elongated, substantially inelastic tube with an elastic balloon tip 14 attached to its distal end, see FIGS. 5A and 5B. The inelastic tube 12 may have multiple ridges 15 disposed along its length extending externally of the tube when the tube has been everted or extended/deployed, such as illustrated in FIG. 5B. Prior to deployment, the ridges may extend inwardly, as the tube is inverted, as illustrated in FIG. 5A. With the ridges extending externally, as in FIG. 5B, the ridges may be exposed to the luminal surface of the Fallopian tube when the sleeve is fully everted. These ridges may increase the ability of the sleeve to gather cells upon balloon retraction, e.g., by additional surface area, and/or frictional contact. In some embodiments, the outer surface of the everted inelastic balloon may be covered with fabric or otherwise textured, as described below, which may increase cell dislodgment and improve cell collection during balloon retraction.

Figure 6A:
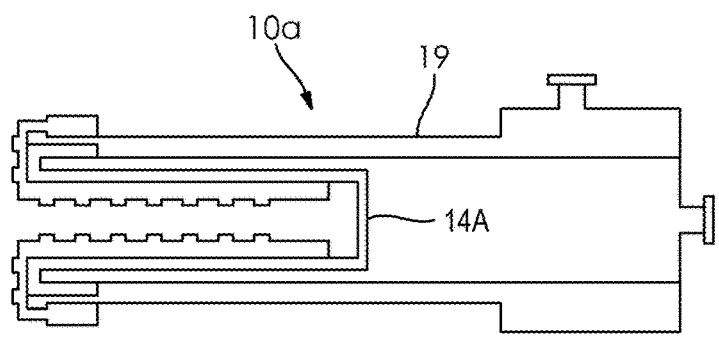
FIG. 6A illustrates a cross-sectional view of an exemplary embodiment of an everting balloon with an outer construction sleeve in a deflated state in accordance with the present disclosure.
Figure 6B:
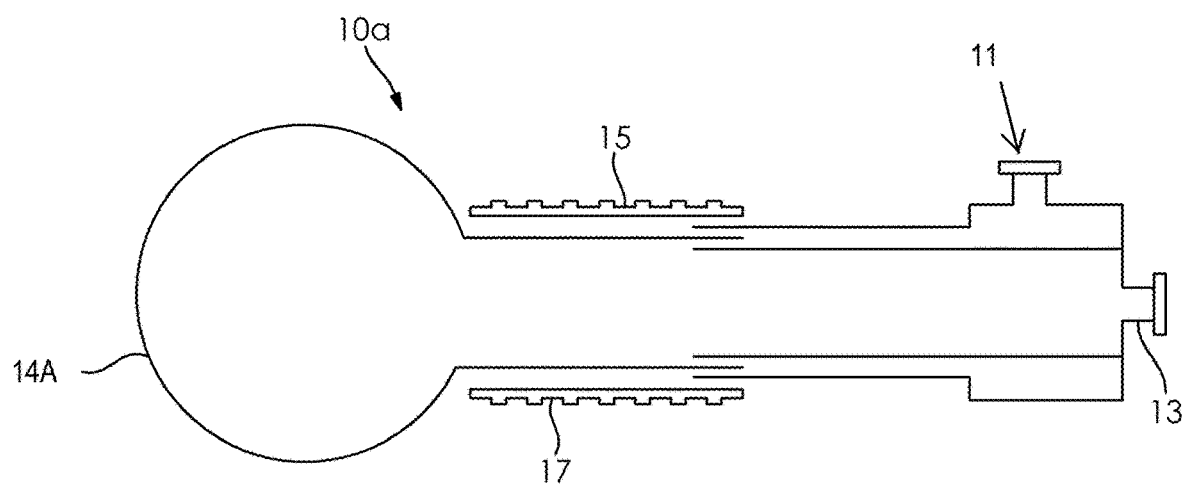
FIG. 6B illustrates a cross-sectional view of the everting balloon with an outer construction sleeve of FIG. 6A in an inflated state in accordance with the present disclosure.
Figure 6C:
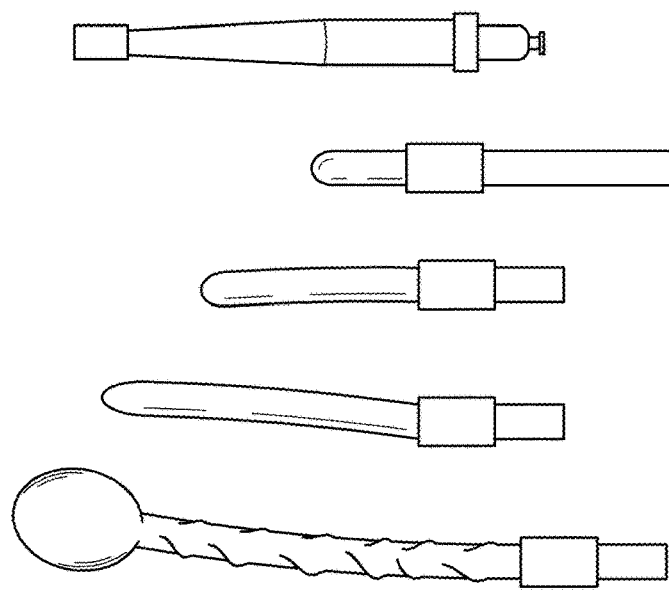
FIG. 6C illustrates an exemplary embodiment of an inflation of the everting balloon with an outer construction sleeve of FIGS. 6A-6B.

FIGS. 6A-6C illustrate an exemplary embodiment of an everting sleeve catheter 10A which may provide protection of a bond between a balloon 14A and a sleeve 17 of the everting sleeve catheter 10A during deployment. The everting sleeve catheter 10A of FIGS. 6A-6C may include an elongated, elastic balloon attachable to a distal tip of the everting sleeve catheter. A substantially inelastic sleeve 17, slightly shorter in length than the elastic balloon 14, may be attached to the elastic balloon 14 at the distal tip of the catheter, and may be invertible so that in an undeployed state, the inelastic sleeve 17 is positioned inside the elastic balloon 14. In response to eversion of the balloon/sleeve combination 14A, 17 the inelastic sleeve 17 may emerge from a double wall 19 of the catheter 10A, so that a portion of the elastic balloon 14A in an extended position is internal to the inelastic sleeve 17, e.g., the inelastic sleeve 17 is disposed on the outside of the elastic balloon 14A and may constrict the elastic balloon 14A along its length, e.g., a majority of its length, to prevent the elastic balloon 14 from expanding and potentially rupturing the Fallopian tube during the time that the everting sleeve is being advanced through the Fallopian tube. Upon full balloon/sleeve eversion, the distal elastic balloon may inflate to approximately 3×-5× the diameter of the sleeve, for occlusion of the distal os upon retraction of the catheter with concomitant pullback of the inflated balloon. In some embodiments, the catheter may contain a port 11 to allow irrigation to occur between the balloon and the inelastic sleeve 17.

Figure 7A:
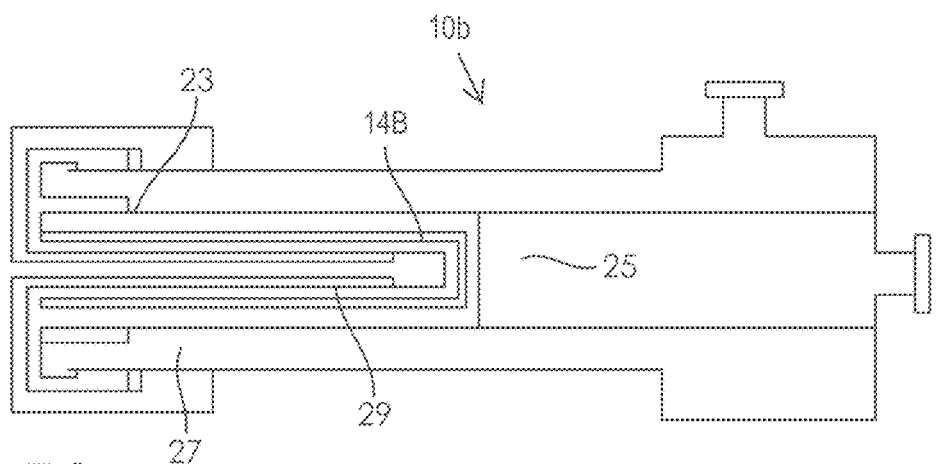
FIG. 7A illustrates a cross-sectional view of an exemplary embodiment of an everting sleeve and elastic balloon with an inelastic delivery balloon in a deflated state in accordance with the present disclosure.
Figure 7B:
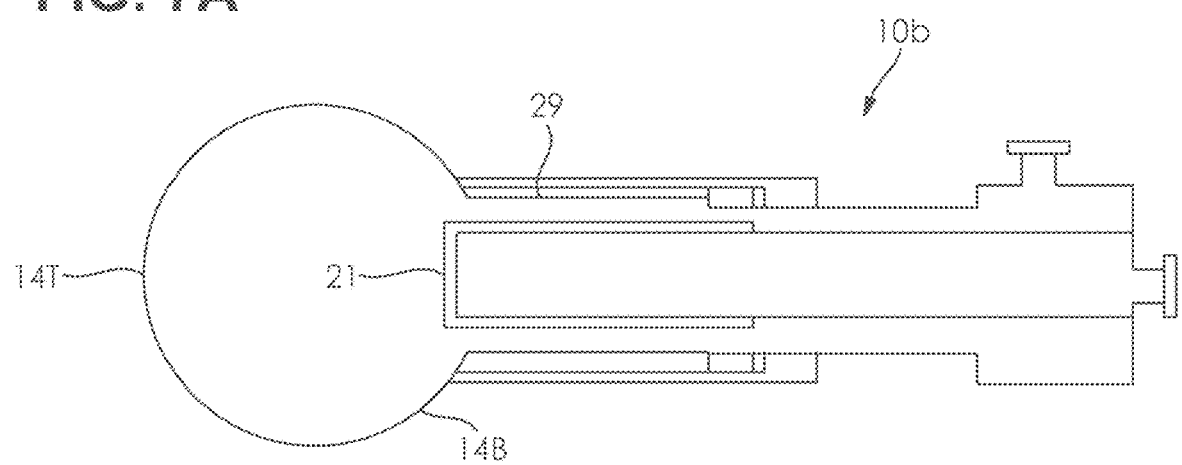
FIG. 7B illustrates a cross-sectional view of the everting sleeve and elastic balloon with an inelastic delivery balloon of FIG. 7A in an inflated state in accordance with the present disclosure.
Figure 7C:
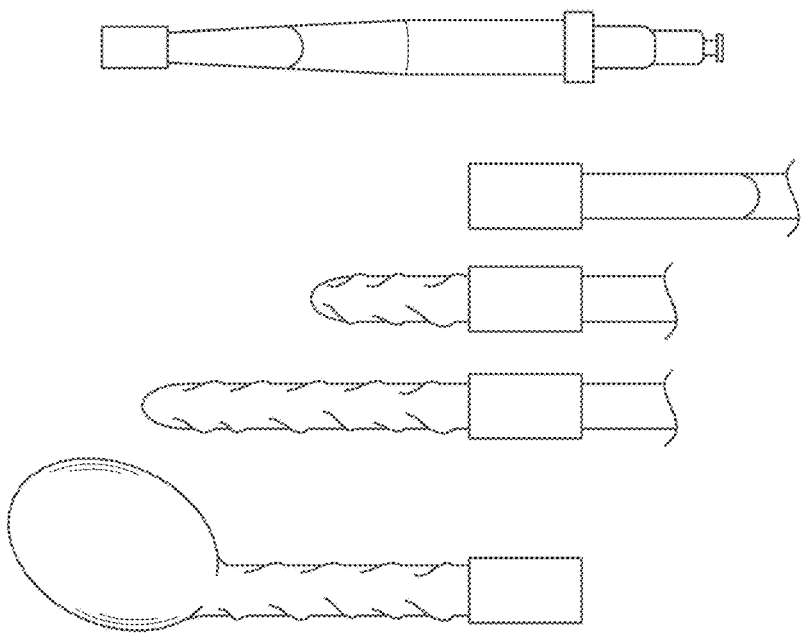
FIG. 7C illustrates an exemplary embodiment of an inflation of the everting sleeve and elastic balloon with an inelastic delivery balloon of FIGS. 7A-7B.

FIGS. 7A-7C illustrate an exemplary embodiment of an everting sleeve catheter 10b including a concentric double walled catheter, and the eversion of three layers are attached to the distal catheter tip. An elongated inelastic balloon 21 may be attached to a distal tip of the inner catheter 23, and the balloon 21 may lie within an inner catheter lumen 25. An elongated elastic balloon 14B, which in some embodiments may be equal in length to the inelastic balloon 21, may be attached to a distal tip of an outer wall 27 of catheter 10b. The balloon 14B may be disposed inside the inelastic balloon 21. An inelastic sleeve 29, which in some embodiments may be shorter in length than the elastic balloon 14B, may be attached to the distal tip of the outer catheter wall 27. The sleeve 29 may be disposed inside the elastic balloon 14B in an undeployed state. Pressurization of the inner catheter 23 may evert the inelastic balloon 21, which may deliver the elastic balloon 14B and outer inelastic sleeve 29. Following full eversion of all three layers, pressurization between the walls of the inner catheter and outer catheter may inflate the elastic balloon 14B. The inelastic sleeve 29 may constrict the elastic balloon 14B along the majority of its length. A distal, un-constricted tip of the balloon 14T may expand to form the occlusion element. This may be advantageous to decrease friction in the system during the eversion process. For example, the inelastic balloon 21 may deliver the elastic balloon 14B and inelastic sleeve 29. The elastic balloon 14B may not undergo expansion until fully everted. In this manner, the elastic balloon 14B may avoid frictional contact with the wall of the inelastic sleeve 29 during eversion, which may be advantageous in facilitating deployment, e.g., when working with small diameter catheters for traversing the Fallopian tube.

Figure 8A:
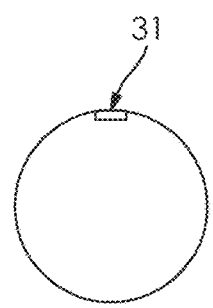
FIG. 8A illustrates a cross-sectional view of an exemplary embodiment of an everting sleeve and elastic balloon with an irrigation lumen in a deflated state in accordance with the present disclosure.
Figure 8A:
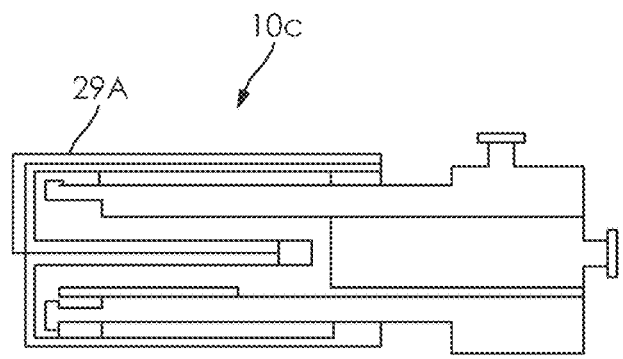
Figure 8B:
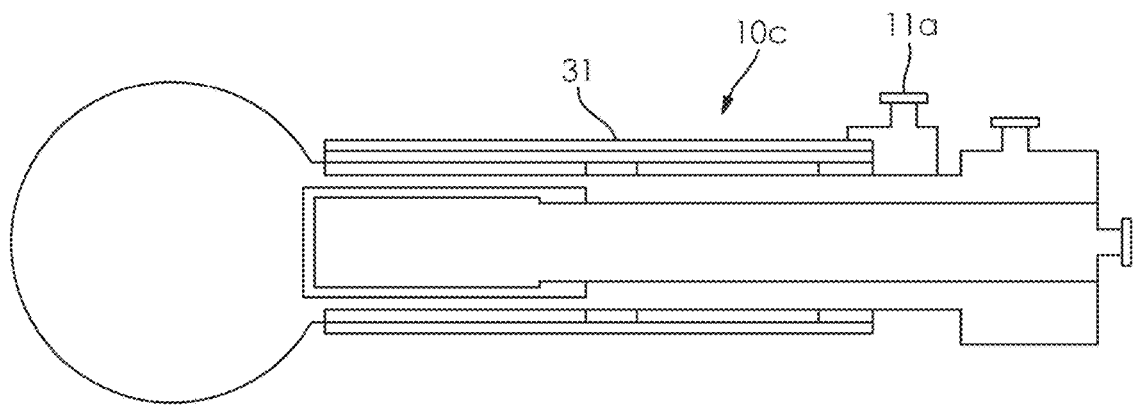
FIG. 8B illustrates a cross-sectional view of the everting sleeve and elastic balloon with an irrigation lumen of FIG. 8A in an inflated state in accordance with the present disclosure.
Figure 9A:
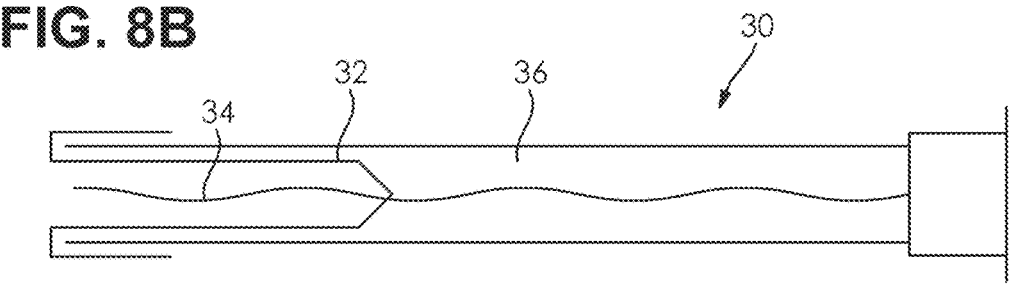
FIG. 9A illustrates a cross-sectional view of an exemplary embodiment of an everting balloon catheter in a deflated state in accordance with the present disclosure.
Figure 9B:
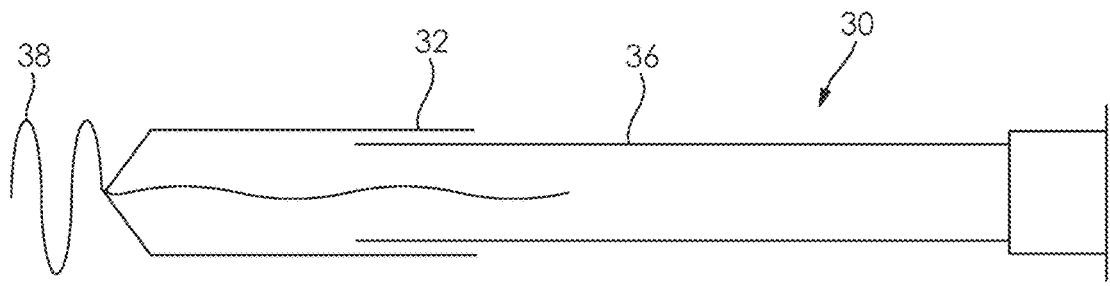
FIG. 9B illustrates a cross-sectional view of the everting balloon catheter of FIG. 9A in an inflated state in accordance with the present disclosure.
Figure 9C:
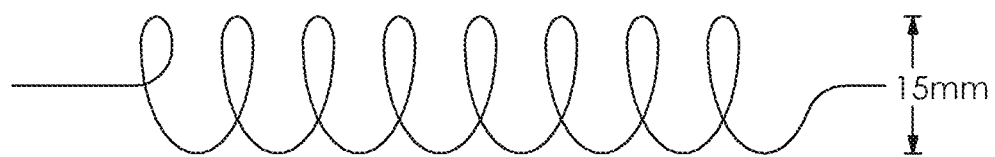
FIG. 9C is an exemplary embodiment of a spiral filament in accordance with the present disclosure.
Figure 10A:
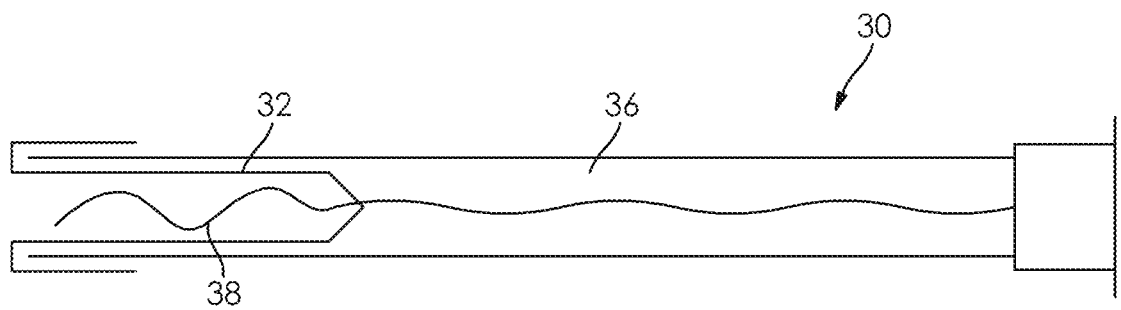
FIG. 10A illustrates a cross-sectional view of an exemplary embodiment of an everting balloon catheter in a deflated state in accordance with the present disclosure.
Figure 10B:
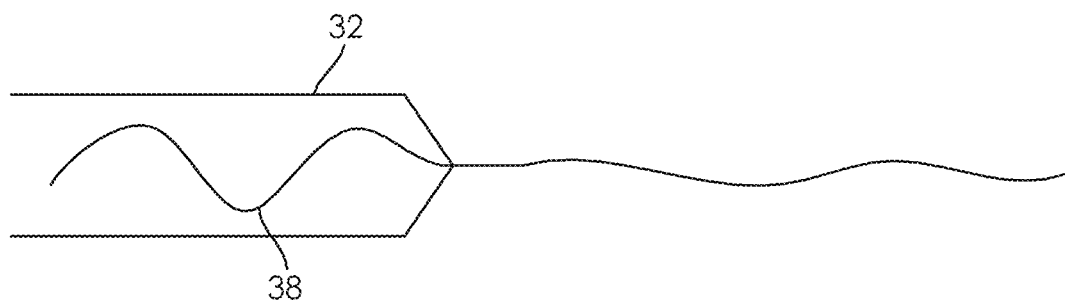
FIG. 10B illustrates a cross-sectional view of the everting balloon catheter of FIG. 10A in an inflated state in accordance with the present disclosure.

FIGS. 8A-8B illustrate an exemplary embodiment of an everting sleeve catheter 10C including an inelastic sheath 29A having a small lumen 31 for irrigation, with the sheath 29A connectable to a third port 11A used for fluid irrigation and aspiration to obtain cytology samples. As noted above, in some embodiments, the irrigation fluid may contain a dye for identification of abnormal and potentially cancerous cells.

Figure 11A:
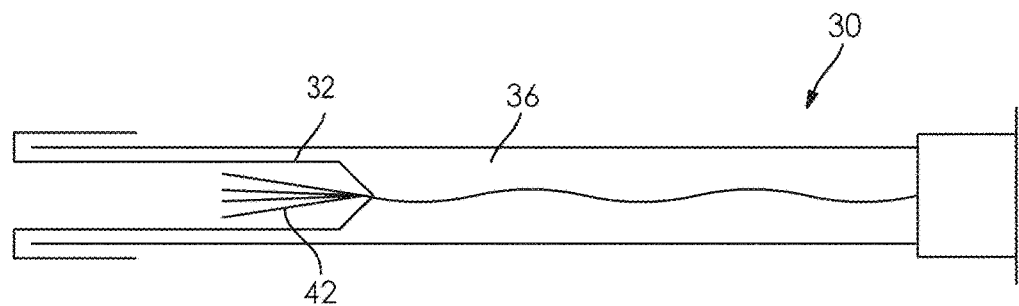
FIG. 11A illustrates a cross-sectional view of an exemplary embodiment of an everting balloon catheter in a deflated state in accordance with the present disclosure.
Figure 11B:
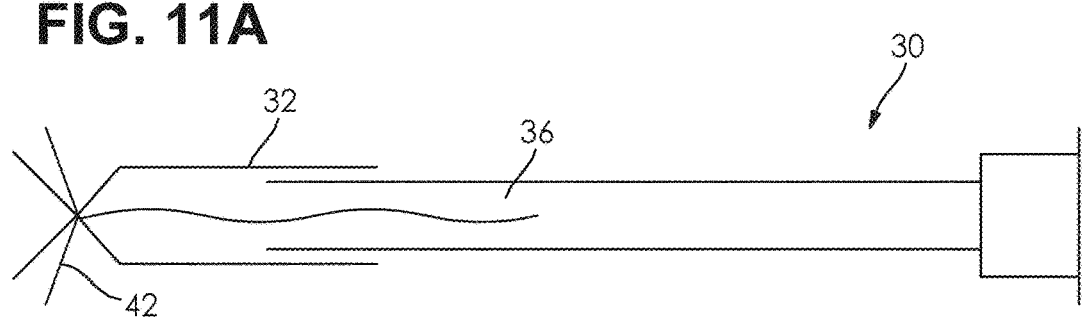
FIG. 11B illustrates a cross-sectional view of the everting balloon catheter of FIG. 11A in an inflated state in accordance with the present disclosure.
Figure 12A:
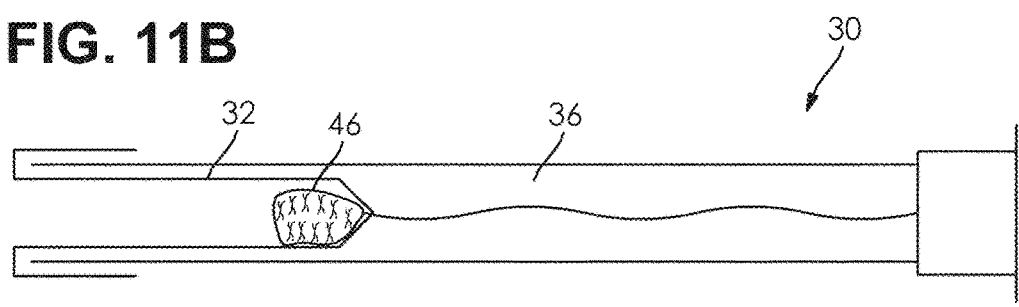
FIG. 12A illustrates a cross-sectional view of another exemplary embodiment of an everting balloon catheter in a deflated state in accordance with the present disclosure.
Figure 12B:
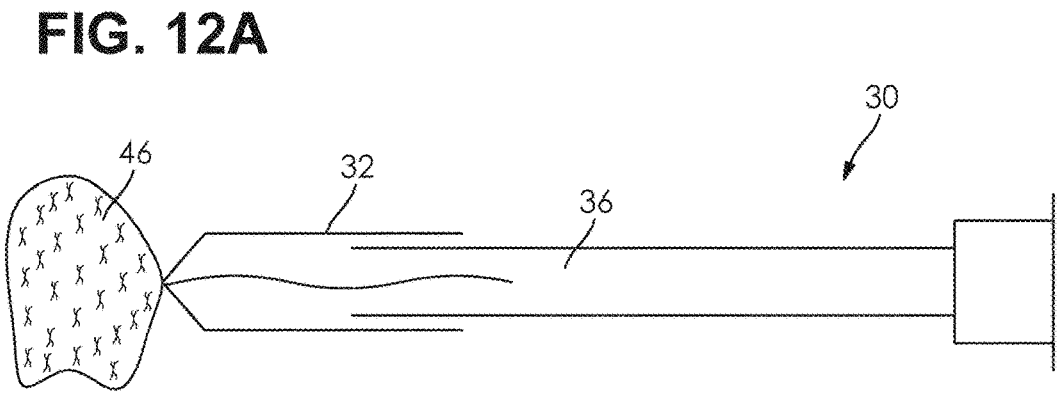
FIG. 12B illustrates a cross-sectional view of the everting balloon catheter of FIG. 12B in an inflated state in accordance with the present disclosure.

Another exemplary embodiment according to the present disclosure is shown in FIGS. 9A-9C and 10A-10B. An elongated balloon 32 including an extending portion 34, e.g., an expandable member, attachable to a distal end of the balloon 32 may be inverted into the lumen 36 of a catheter 30. In an inverted, e.g., undeployed state, the extending portion 34 may lie inside the elongated balloon 32. In some embodiments, the extending portion 34 may be a spiral of one or more loops of filament 38. The filament that forms the extending portion 34 may be formed from a variety of materials illustratively including a monofilament polymer material such as Nylon or polypropylene, fluoropolymers, or polylactic acid; metal such as stainless steel titanium, or platinum; or a superelastic metal such as Nitinol, or combinations thereof. In some embodiments a fiducial marker may be included on the filament and/or balloon and deliverable to the Fallopian tube (not shown) to facilitate subsequent return to the situs of cell sampling. It may be appreciated that the extending portion may also have alternative configurations, such as an expandable member. The extending portion 34 e.g., expandable member, may contain a plurality of outwardly oriented bristles 40 formed of polymer or metal (see FIG. 18). In some embodiments, the extending portion 34 may be included as an elongated strand 38 of material that curls, spreads or fans out 42, balls up 44 to a predetermined shaped when released from being constrained inside the catheter (FIGS. 11A-11F or FIGS. 14A-14B), or combinations thereof. In some embodiments, the extending portion 34, e.g., expandable member, may be formed of a compressed polymer foam that self-expands upon release into a wet environment (FIGS. 12A-12B). Upon pressurizing the catheter adjacent to the proximal os, the balloon 32 may evert so as to urge the inverted portion outward into the extended position and into contact with the Fallopian tube inner wall cells. In some embodiments, upon full balloon eversion, the extending portion 34 may be extended out of the distal os of the Fallopian tube and into the abdominal cavity. In some embodiments, the extending portion 34 may have an expanded outer diameter of approximately 5-15 mm.

Figure 18:
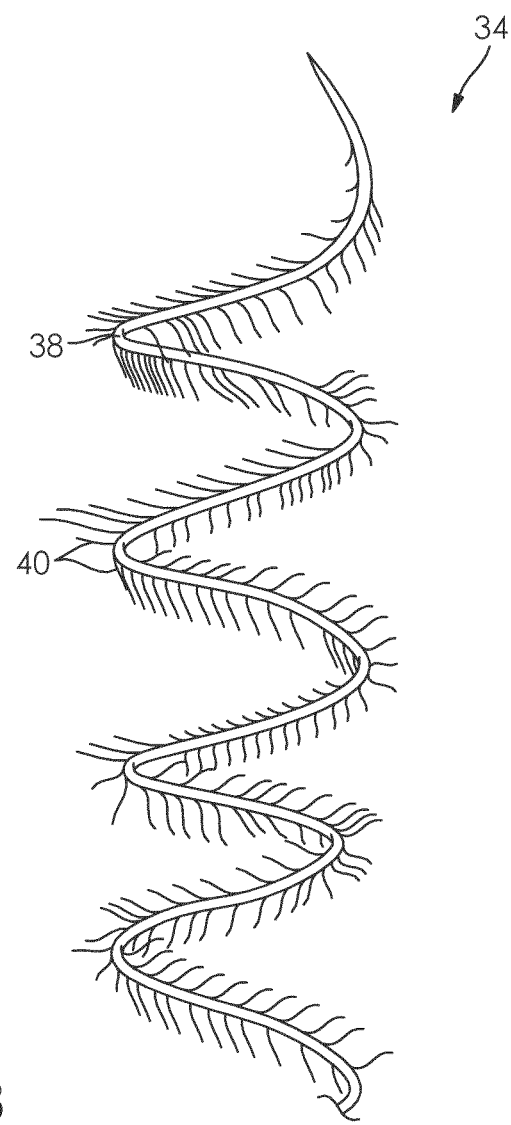
FIG. 18 illustrates an exemplary embodiment of an extending element in accordance with the present disclosure.
Figure 19:
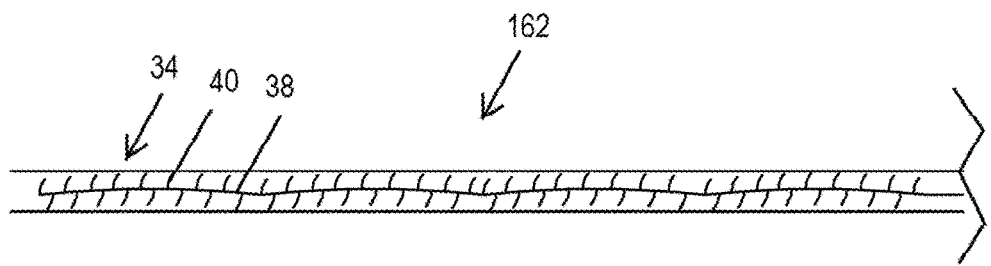
FIG. 19 illustrates an exemplary embodiment of an extending portion in a retracted state after cell collection in accordance with the present disclosure.
Figure 20:
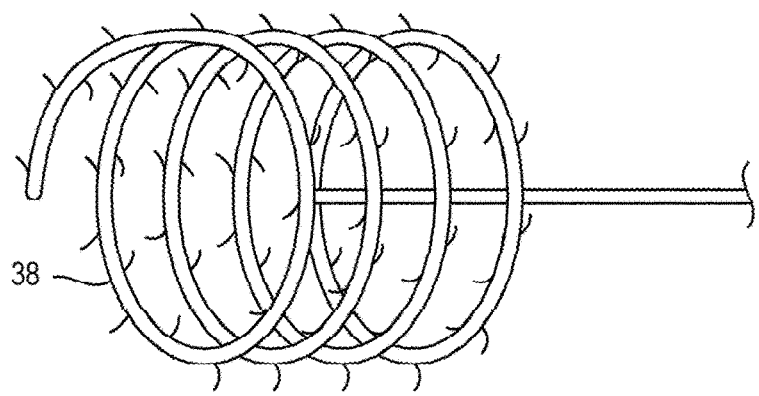
FIG. 20 illustrates the separate extending portion of FIG. 19 in a deployed state in accordance with the present disclosure.

An advantage of the extending portion 34 having a plurality of bristles is that there may be added surface area on which a sample (e.g., cells and/or tissue) is collectable, including areas that are not likely to be exposed to shear forces when the device is retracted back within the catheter. Cell collection may therefore be maximized, as well as minimizing an amount of cells that are wiped off when the device is pulled through the Fallopian tube or into a sheath, as seen in FIGS. 18-20. In those embodiments in which the extending portion has a greater surface area, the cell collection may increase per linear unit of Fallopian tube so engaged under like pressurization conditions, as compared to a contourless extending portion.

Figure 13A:
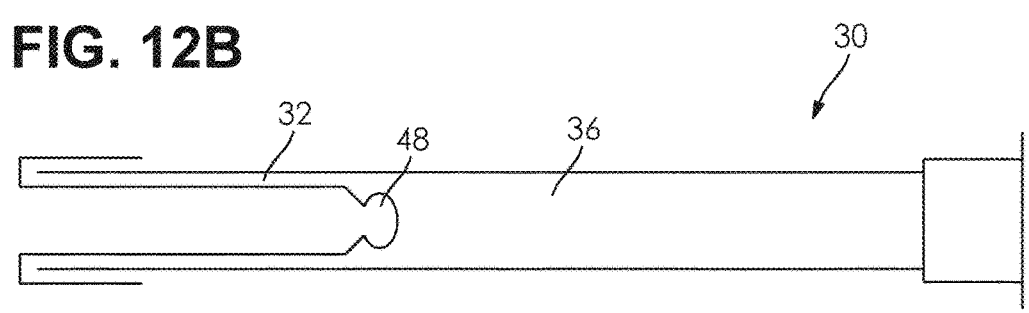
FIG. 13A illustrates a cross-sectional view of another exemplary embodiment of an everting balloon catheter in a deflated state in accordance with the present disclosure.
Figure 13B:
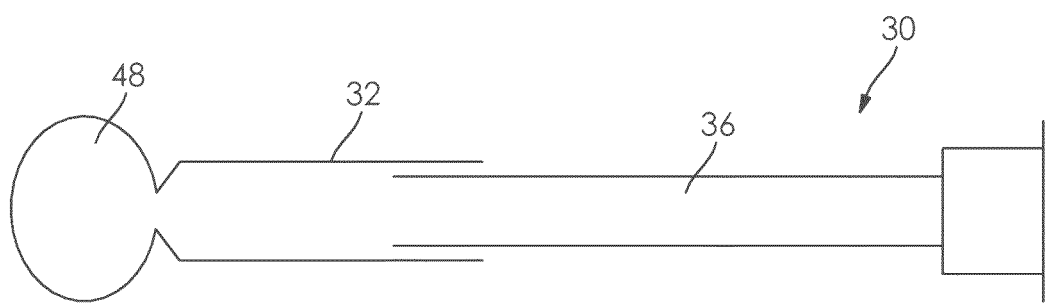
FIG. 13B illustrates a cross-sectional view of the everting balloon catheter of FIG. 13A in an inflated state in accordance with the present disclosure.
Figure 14A:
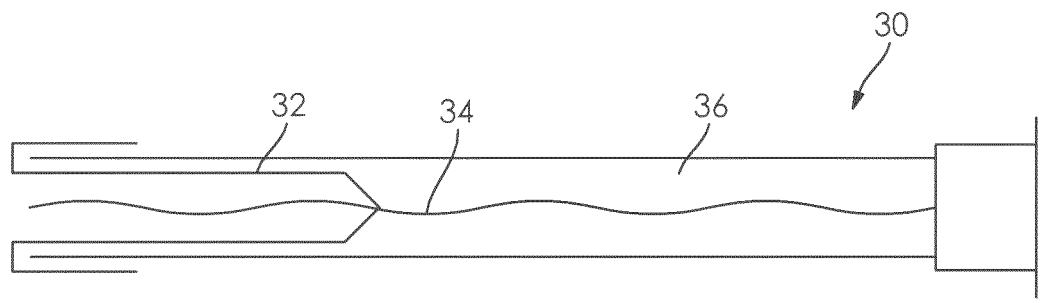
FIG. 14A illustrates a cross-sectional view of another exemplary embodiment of an everting balloon catheter in a deflated state in accordance with the present disclosure.
Figure 14B:
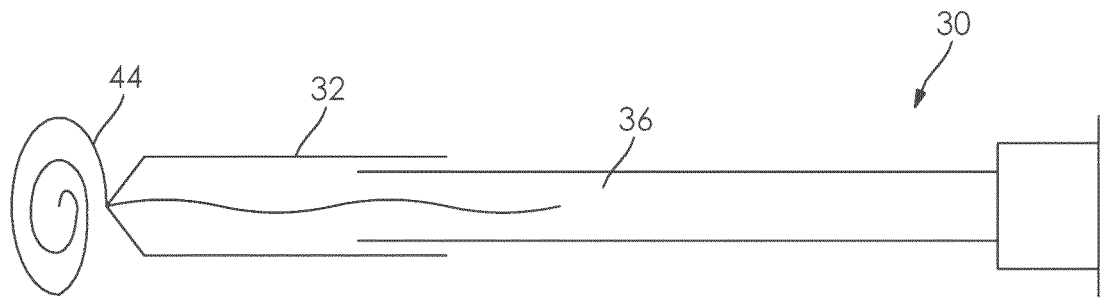
FIG. 14B illustrates a cross-sectional view of the everting balloon catheter of FIG. 14A in an inflated state in accordance with the present disclosure.
Figure 15A:
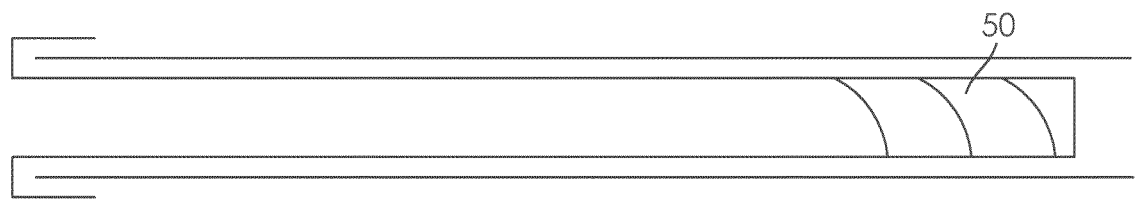
FIG. 15A illustrates a cross-sectional view of an exemplary embodiment of an everting balloon spiral cannula in a deflated state in accordance with the present disclosure.
Figure 15B:
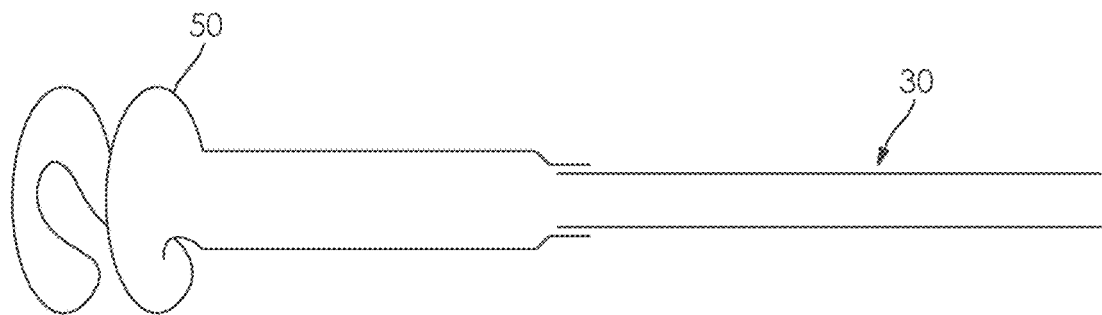
FIG. 15B illustrates the everting balloon spiral cannula of FIG. 15A in an inflated state in accordance with the present disclosure.
Figure 16A:
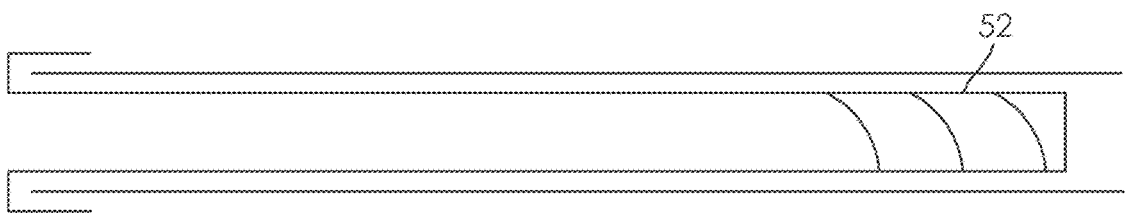
FIG. 16A illustrates a cross-sectional view of an exemplary embodiment of an everting distal arc balloon cannula in a deflated state in accordance with the present disclosure.
Figure 16B:
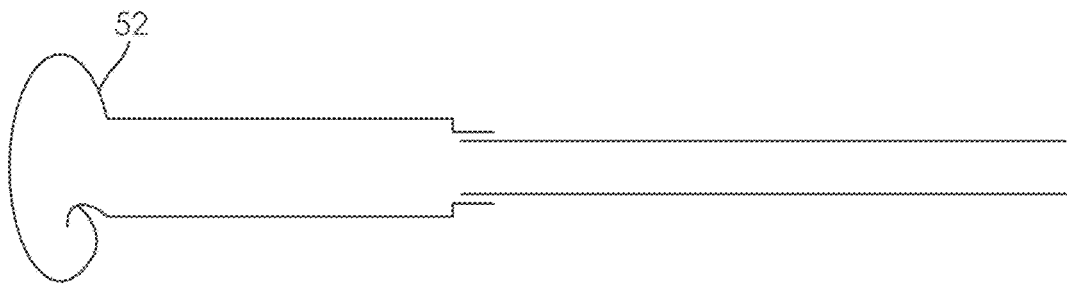
FIG. 16B illustrates the everting distal arc balloon cannula of FIG. 16A in an inflated state in accordance with the present disclosure.

In still other embodiments of a catheter in accordance with the present disclosure, the extending portion, e.g., expandable member, may form any number of shapes and contours. For example, multiple filaments 42 may be attached to the distal end of the balloon 32 that splay out upon balloon eversion to form a brush 42 (FIGS. 11A-11B). In some embodiments, a braided string or suture 43 may be extendable distally of the balloon 32 upon eversion (see FIGS. 11C-11D), and in other embodiments, the braided suture may be formed of various materials and/or may be one or more colors for visual confirmation of extension of the suture 43 (see FIGS. 11E-11F). A polymer foam structure 46 may be compressed inside the balloon 32, and may self-expand in response to balloon 32 eversion and exposure to a fluid environment (FIGS. 12A-12B). An elastic or inelastic balloon 48 may be disposed on the distal end of the inelastic sleeve balloon 32 (FIGS. 13A-13B). Alternatively or additionally, embodiments may include an everting balloon having a superelastic wire coil (FIGS. 14A-14B), a spiral everting balloon 50 (FIGS. 15A-15B), an everting distal arc balloon 52 (FIGS. 16A-16B), or a long elastic filament of polymer or metal that gathers into a three-dimensional structure upon balloon eversion, such as an inner lumen 54 (FIGS. 17A-17B), and expandable member 34 having a plurality of outwardly oriented bristles 40 (FIG. 18), or combinations thereof. It may be appreciated that any of these embodiments of a catheter extending portion as an expandable member or otherwise may include a fiducial marker as a navigation aid for a medical professional to navigate back to a desired situs in the Fallopian tube. For example, a marker may be deliverable to a desired location in a Fallopian tube, e.g., through an inner lumen 54, or by a balloon 32. Such markers are known to the art and illustratively include radio-opacity markers, isotopic markers, and radiofrequency markers. In still other embodiments, a biodegradable extending portion or a permanent extending portion may be severable from the catheter. In still other embodiments, the extending portion may deliver a therapeutic agent such as a chemotherapeutic drug, antibiotic, anti-inflammatory, or combinations thereof, of the Fallopian tube tissue.

When the catheter is retracted back into the working channel of the hysteroscope, cells may be dislodged from at least a portion of the entire length of the inner surface of the Fallopian tube. In some embodiments, the extending portion may be inverted back within the balloon by reducing the gas pressure within the balloon, and reinverting the balloon within the catheter tip region, so as to shield collected cells with the catheter tip region internal bore. In other embodiments, the extending portion and balloon, in either a deflated state or remaining inflated, may be retractable back within a sheath without the balloon being reinverted. For example, as shown in FIG. 19, an extending portion 34, e.g., an expandable filament 38 including a plurality of bristles 40, may be protected during removal from the patient by a sheath 162 (see FIG. 23A).

An extending portion 34, e.g., an expandable filament 38 as shown in FIGS. 18-20, may be attached to an end of the inverting balloon. In some embodiments, an extending portion 34, e.g., expandable coil, may be connected to the push wire (see FIG. 23A). In some embodiments, the extending portion may be connected to a distal end of the push wire 134. In some embodiments, an extending portion 34 (e.g., spiral) may be a collection device passed through an inner lumen that may expand upon reaching the distal end into the Fallopian tube. It may be appreciated that cells may be collectable from a specific portion of the Fallopian tubes, for example the fimbria, and then protected by a sheath 162 so as to minimize potential for distal cells to be wiped off by the inner surface of the proximal Fallopian tube as the device is removed.

In some embodiments, friction between an outer surface of the extending portion 34, e.g., an expandable filament 38, and an inner lining of the Fallopian tube is sufficient to dislodge cells and adhere such cells to the expandable member, even in embodiments having a contourless extending portion. For example, an expanded spiral at the distal end of the balloon may contact the fimbria at the distal end of the Fallopian tube to collect cell samples. Since the Fallopian tube increases in inner diameter as it proceeds from its proximal to its distal end, expansion of the extending portion 34, (e.g., by the expandable filament 38) may maximize obtained cell samples at the distal end of the Fallopian tube (e.g., fimbrial portion of the Fallopian tube).

The elongated balloon and the extended portion may in some embodiments be retractable into the working channel of the hysteroscope to avoid loss of cell samples as the hysteroscope is removed from the patient. An elastomer seal at the proximal end of the working channel of the hysteroscope may seal against an outer surface of the catheter. This seal may act to deter the catheter from sliding from a desired position within the working channel of the hysteroscope, or from sliding completely out of the working channel A mark on the catheter body may indicate a length of retraction necessary to ensure that the elongated balloon and distal spiral are fully within the hysteroscope working channel. Upon removal of the hysteroscope from the patient, in some embodiments, a syringe containing saline solution may be attached to the Luer fitting at a proximal end of the working channel Saline may be used to flush cells gathered by the elongated balloon and expanding spiral into a test tube. It may be appreciated that the cells collected by the expandable member may be collected for testing by conventional techniques and may be prepared for cytological, molecular or genetic examination.

Figure 17A:
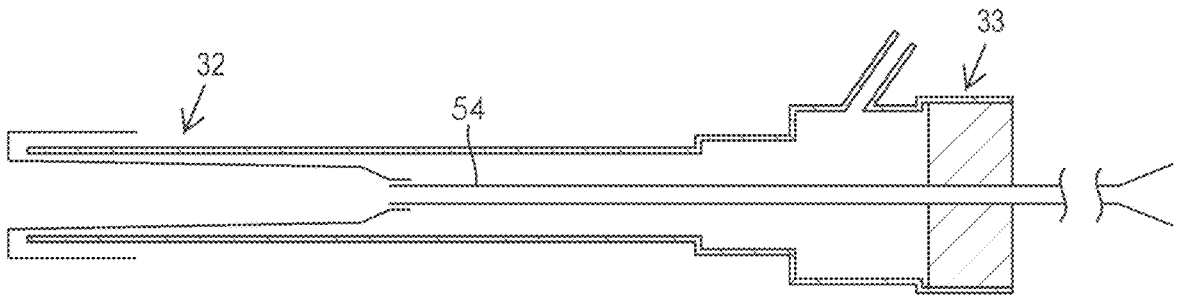
FIG. 17A illustrates a cross-sectional view of another exemplary embodiment of an everting balloon catheter in a deflated state in accordance with the present disclosure.
Figure 17B:
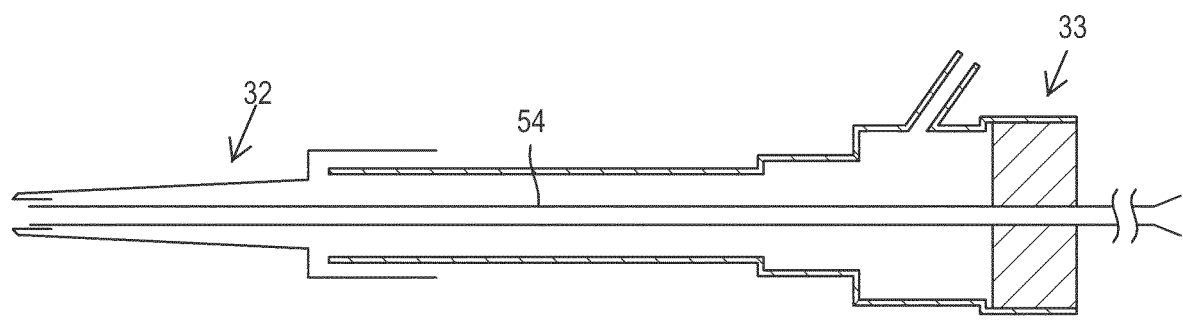
FIG. 17B illustrates the everting balloon catheter of FIG. 17A in an inflated state in accordance with the present disclosure.

In some embodiments, an inner lumen 54 may be formed of a material having sufficient rigidity to maintain an opening in the lumen. For example, the inner lumen 54 may be sufficiently rigid to withstand a pressure of the balloon as it is inflated and everted. In embodiments, the inner lumen 54 may be formed of a metal, composite, or polymer, or combinations thereof, including a polyethylene terephthalate (PET) material and may be attached to the catheter, as shown in FIGS. 17A-17B. The eversion process follows that of the aforementioned embodiments having a push wire that does not include a lumen. This embodiment may also include an inflation sideport and a proximal seal 33 that may allow the balloon 32 to be everted while maintaining an orifice through the inner lumen 54 in fluid communication between the hysteroscope and the patient body tissue. Once everted, the inner lumen 54 may provide a pathway through which a separate extending portion may be passed, or a surgical instrument package or visualization device may be passed. In some embodiments, various agents may be brought into contact with the lumen via the pathway. These agents and rationales therefore may illustratively include microbubbles to serve as acoustic contrast agents, contrast dyes for various forms of spectroscopic imaging, or therapeutics for treating cells or killing cancerous cells, or combinations thereof. Therapeutics may illustratively include antibodies specific to cancerous cells and carrying a chemotherapeutic or radio-isotope, chemotherapeutics, radio-isotopic seeds, antibiotics, antifungals, or combinations thereof.

Figure 21A:
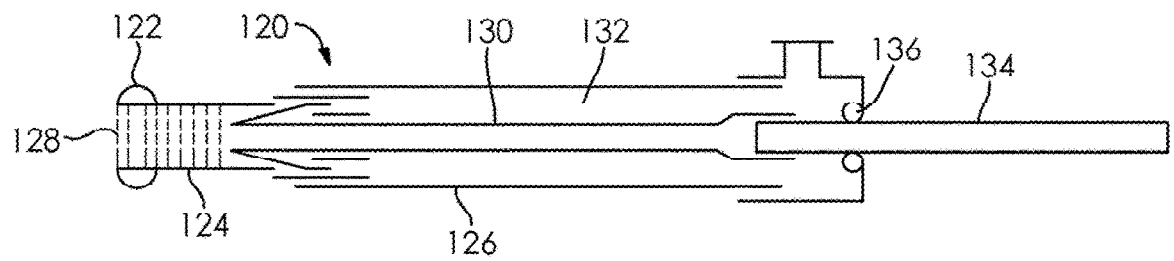
FIG. 21A illustrates a cross-sectional side view of an exemplary embodiment of a ball tip everting balloon catheter prior to deployment of the balloon in accordance with the present disclosure.
Figure 21B:
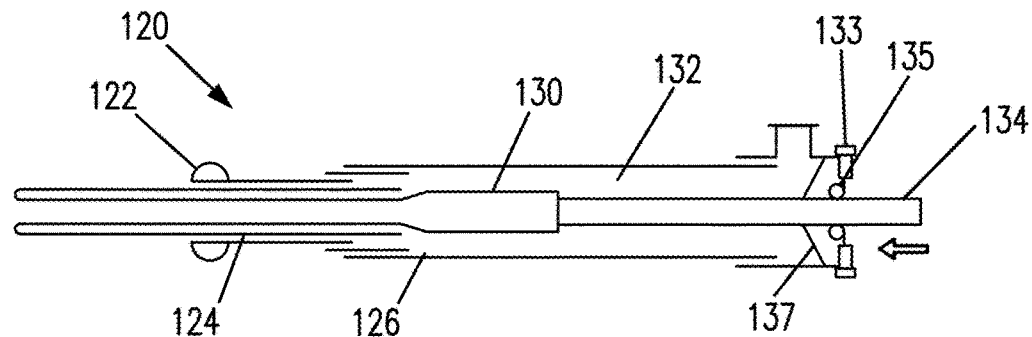
FIG. 21B illustrates a cross-sectional side view of an exemplary embodiment of the ball tip everting balloon catheter of FIG. 21A in a deployed state in accordance with the present disclosure.

FIGS. 21A-21B illustrate cross-sectional views of an exemplary embodiment of a ball tip everting balloon catheter 120 in accordance with the present disclosure. A spherical ball 122 may be attached to the distal end of a spring tip 124 affixed to a tube, or catheter 126. It is understood that "tube" and "catheter" 126 may be used interchangeably. The spherical ball 122 may be provided to negotiate through a patient's UTJ to minimize and/or avoid inadvertent penetration through the UTJ sidewalls. The spring tip 124 may allow the distal end with the ball 122 to flex around corners and navigate through the UTJ. The spring tip 124 and spherical ball 122 may have an open lumen 128 extendable through the spring tip 124 and the spherical ball 122. The spherical ball 122 on the spring tip 124 may be approximately 0.8-1.0 mm in diameter, and the hollow spring tip 124 may have a length of approximately 1.5 cm and an outer diameter of approximately 0.6 mm. The hollow spring tip 124 may be formed of a metal (stainless steel or superelastic metal, e.g., Nitinol) coil spring sheathed on the outside with thin walled polymer heat shrink tubing, made of nylon, PET (polyethylene terephthalate), or similar material. In some embodiments, the spring tip 124 may be a metal coil spring co-extruded into a tubular polymer body. The hollow spring tip 124 may also be a flexible polymer tube, and in some embodiments may be made of nylon, Polyethylene terephthalate (PET), polyether block amide, or similar materials. An everting balloon 130 may lie inside the hollow spring tip 124. The everting balloon 130 may extend proximally inside the main lumen 132 of the introduction catheter 126 (e.g., a generally flexible tubular structure) or cannula (e.g., a generally rigid tubular structure).

The proximal end of the everting balloon 130 may be attached to a push rod 134 passable through a seal 135 on the proximal end of the catheter 126 or cannula. In operational use on a patient, the flexible ball tip 122 may be manually advanced through the UTJ. Once passage of the flexible ball tip 122 and spring tip 124 through the UTJ occurs, the push rod 134 may be advanced through the seal 135 of the previously pressurized introduction catheter 126 or cannula. Advancement of the push rod 134 may cause a controlled eversion of the balloon 130 out of the hollow spring tip 124, through the length of the Fallopian tube.

Figure 23A:
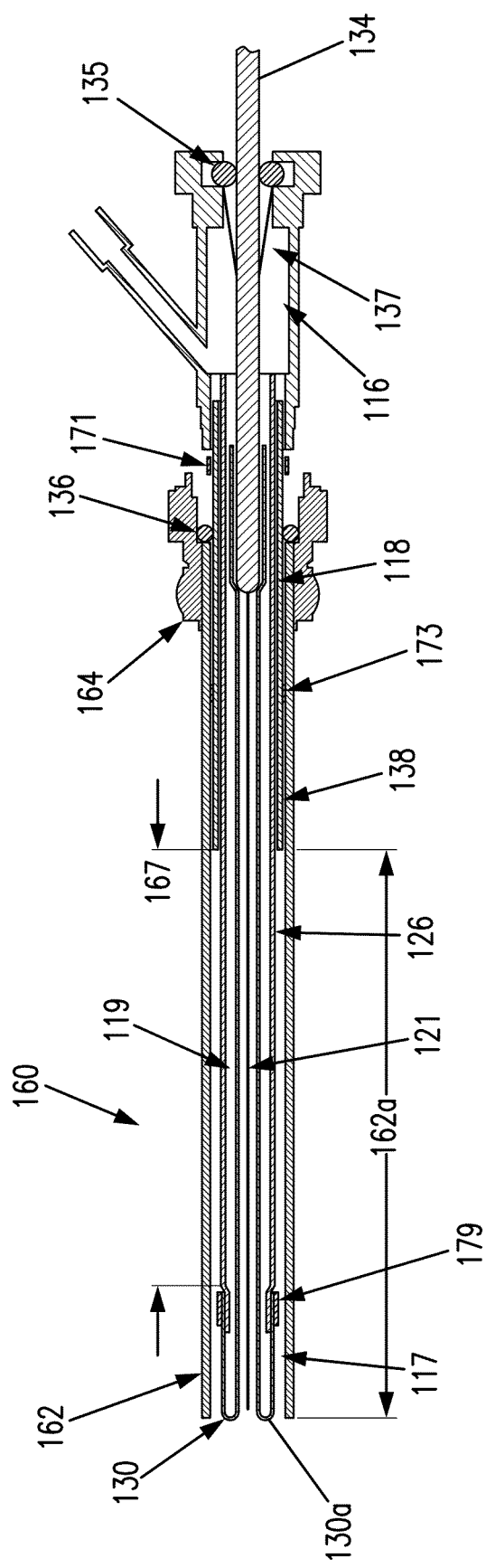
FIG. 23A illustrates a cross-sectional side view of an exemplary embodiment of a balloon tip catheter in accordance with the present disclosure.

According to some embodiments, a seal 137 may be disposed within the tube/catheter shaft 126 through which the push wire 134 passes as the push wire 134 actuates the balloon (see FIGS. 21B, 23A). In some embodiments, the seal 137 may be a conical seal disposed between a pressurized chamber 116 and the push wire 134. It is noted that the terms "push wire" and "push rod" are used herein synonymously. The conical seal 137 may allow the push wire 134 to advance through the catheter 126 to actuate the balloon 130 between an inverted position and an everted position while maintaining pressure in the catheter 126. Various embodiments of the present disclosure may provide an adjustable seal 135, disposed proximal to the conical seal 137. In response to a leak forming between the push wire 134 and the conical seal 137, the adjustable seal 135 may be adjusted to maintain the pressure required to move the balloon between the first inverted position and the second everted position. The adjustable seal 135 may be a rotating hemostasis valve, e.g., a device for maintaining seals between coaxial devices, and adjustable by knob 133. In some embodiments, a hemostasis valve may be used as seal 135. The hemostasis valve may include a compressible gasket to provide a desired degree of sealing.

The knob 133 may be rotatably adjustable to adjust the seal 135. In use, a user may be able to adjust the knob 133 to tighten or loosen the knob 133. By tightening the knob 133, the seal 135 may be compressed, thereby collapsing around the push wire 134. The rotatable knob 133 may provide the user with improved control over the seal and the ability to react if there are any leaks from the conical seal 137.

In embodiments, the elongated balloon may be initially inverted into a catheter lumen during assembly, e.g., the balloon may be turned inside out during assembly. The balloon may be pressurized to deploy, so that the balloon everts and "unrolls" into the Fallopian tube. The unrolling mechanism of the eversion may track through the Fallopian tube regardless of tortuosity or constriction in the Fallopian tube. A great majority of the length of the balloon may be substantially inelastic, e.g., up to 100% of the length of the balloon, such that the balloon may not substantially expand and dilate as it everts, e.g., so the Fallopian tube may not expand or dilate as the balloon everts. In other embodiments, a portion of a distal end of a balloon may be expandable into the fimbriated end of the Fallopian tube (e.g., see FIGS. 5-8). Balloon overexpansion may burst or injure the Fallopian tube.

An exemplary process common to the various embodiments of devices may include the deployment of the distal end of a catheter. In some embodiments, a catheter distal end may be delivered to a proximal end of the Fallopian tube by a conventional hysteroscope. Regardless of the mode of deployment, a retracted portion of the balloon inside of the catheter shaft 126 may be extendable from within the catheter shaft 126 into contact with an interior wall of the Fallopian tube. It has been surprisingly found that the act of extending the portion may abrade a sufficient amount of cells and/or tissue from the Fallopian tube wall to perform histological evaluation. This is observed for planar surfaces of a balloon of seemingly non-abrasive character. While a roughened surface texture on the balloon may be included for contacting the Fallopian tube wall in some embodiments, the surface of the inelastic balloon portion may be sufficient to dislodge a sufficient amount of cells and/or tissue for statistically meaningful histological evaluation regardless of whether the balloon is fully inflated or partially deflated and crinkled. It has also been surprisingly found that withdrawal of the extended portion may removes still more cells. In other embodiments, the extended portion may be retracted prior to catheter removal so as to preclude dispersal of dislodged Fallopian tube cells to surrounding tissue. Upon catheter removal, contacting the exposed portion of the extended portion, now covered in cells with a microscope slide or other diagnostic substrate, may be sufficient to test for abnormal cells and in particular cancerous cells.

The catheter 126 described above, and in greater detail below may be introduced into the uterus of a patient using an operating hysteroscope 20, an example of which is shown in FIG. 3. An operating hysteroscope 20 may include one or more working channels. One working channel may provide irrigation to distend the uterus and allow endoscopic visualization, and one or more additional working channels may allow instruments and/or catheters to be advanceable distally of the hysteroscope. The catheter 126 (e.g., FIGS. 21A and 21B) may be advanceable through the working channel of the operating hysteroscope, and may cannulate the proximal os of a Fallopian tube. The everting balloon 130 may be advanced through the proximal catheter 126 into the proximal portion of the Fallopian tube.

Figure 22A:
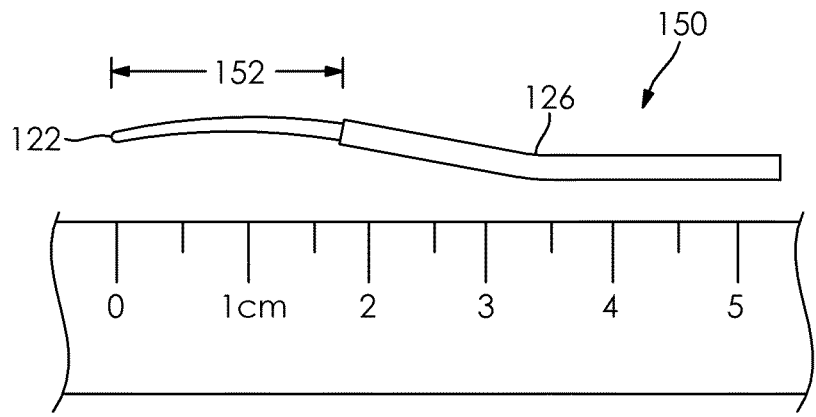
FIGS. 22A-22C illustrate an exemplary embodiment of an everting balloon exiting from a catheter in accordance with the present disclosure.
Figure 22B:
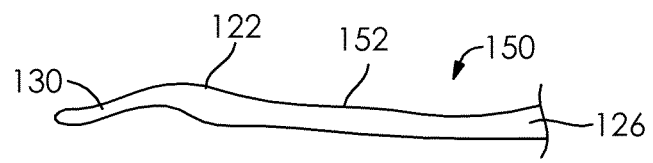
Figure 22C:
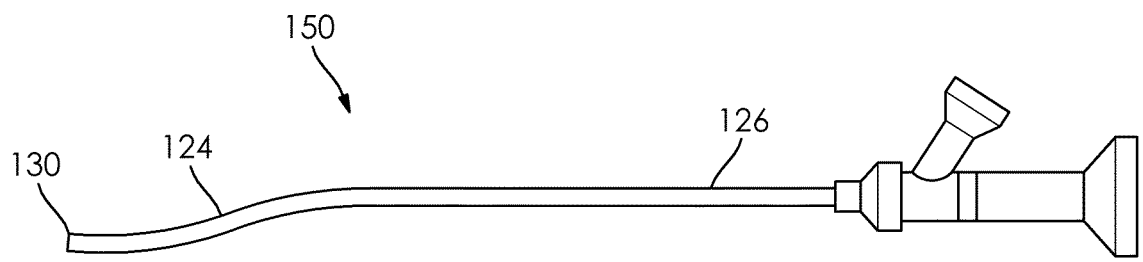

FIGS. 22A-22C illustrate an exemplary embodiment of an everting balloon 130 exiting from a flexible tip 152 with a spherical ball 122 in accordance with an embodiment of the disclosure. The nylon flexible tip 152 and spherical ball 122 may be configured to pass through the patient UTJ for the deployment of the everted balloon 130 in the Fallopian tube. In an embodiment, a ball tip everting balloon catheter 150 may be configured with approximately a 0.9 mm ball tip on approximately 0.66 mm dia.×18 mm long tip. In some embodiments, the tip may be formed of nylon. In some embodiments, a 4 Fr catheter with a 0.64 mm diameter balloon that may evert through and beyond the tip.

Figure 23B:
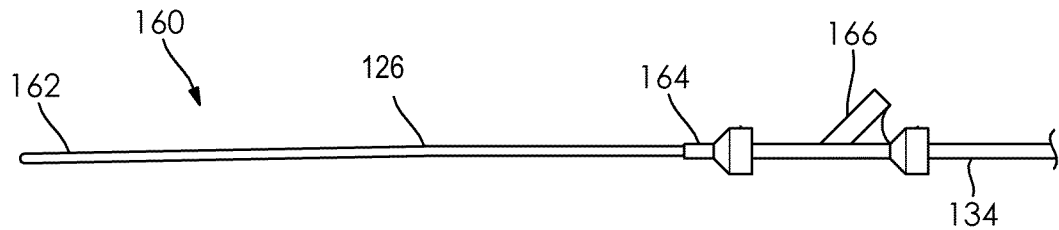
FIG. 23B illustrates the balloon tip catheter of FIG. 23A in accordance with the present disclosure.

FIGS. 23A-23B illustrate a cross-sectional side view of a balloon tip catheter, or device, 160 in accordance with the present disclosure. In some embodiments, a balloon 130 may have an outer diameter of approximately 0.8-1.0 mm, and may have an initial everted length of approximately 1-3 cm, e.g., approximately 1.2-1.5 cm extending out of the distal end of the catheter 126 or cannula. The balloon 130 may be fully evertible into the Fallopian tube, e.g., extending approximately 7-12 cm. The balloon 130 may be securable to a distal end of the catheter shaft or tube 126, as indicated at reference numeral 117, and a push wire 134, as indicated at reference numeral 118. For example, the distal end 118 of the push wire 134 may form an end of the balloon 130. In embodiments, the balloon 130 may be bonded to the distal end 118 of the push wire 134. The push rod or wire 134 may actuate the balloon 130 from an inverted position in the catheter 126 to an everted position when an interior of the balloon, between the catheter 126 and the balloon 130 and indicated by reference numeral 119, is pressurized. In embodiments, an everted position may include at least a portion of the balloon 130 extending beyond the distal end of the tube 126. In some embodiments, the balloon 130 may be initially partially everted and fixed to the catheter 126, forming a rounded end 130a. In some embodiments, the balloon 130 may be inflatable with fluid to a pressure of approximately 14-24 atm (206-353 psi).

In some embodiments, as described above, the device 160 may include a sheath 162. The sheath 162 may be coaxial with the catheter 126. The sheath 162 may be slidably adjustable relative to the catheter 126 to cover at least a first length of the balloon 130 extending outward from the distal end of the tube 126 in an everted position. The sheath 162 may form a physical barrier between the balloon 130 and the interior of the scope to protect the balloon. For example, an initial length, e.g., approximately 1.5 cm of the balloon 130, may be extended from the catheter 126 during insertion through the scope. As the balloon is actuated (e.g., via the push wire 134 and/or balloon pressurization), the sheath 162 may protect the balloon in at least one of the inverted position, a partially everted position, or a fully everted position, or combinations thereof.

The sheath may also act to provide column strength to the balloon as it is everted. In some embodiments, a portion of the sheath 162 may be at least partially translucent, optically transparent, or combinations thereof, as indicated at reference numeral 162a. In embodiments, the transparent portion 162a of the sheath 162 may at least partially overlap with a transparent portion 167 of the catheter 126. For example, a medical professional may be able to visualize the balloon 130 (e.g., to confirm positioning and/or full balloon extension) with the hysteroscope 20 through at least a portion of the sheath 162 and/or the catheter 126. In some embodiments, the catheter may include a sheath knob 164 located at a proximal end of the sheath 162 to connect the sheath 162 to the tube 126.

The pressurized balloon 130 may have a rounded end 130a for atraumatic cannulation of the proximal os and advancement within the Fallopian tube and a degree of flexibility along the balloon 130 length. The balloon 130 may have sufficient column strength to allow the balloon 130 to be manually advanced through the UTJ, for example, with a push wire 134, under at least a partial pressure or no pressure. In some embodiments, the balloon 130 may be constructed of a thin-walled polymer material, such as polyethylene terephthalate (PET), polyethylene, Nylon, polymer, or a similar material. The balloon 130 may have a wall thickness from approximately 0.0001 to 0.001 inches and in some embodiments between approximately 0.00019 and 0.00031 inches. In some embodiments, the balloon 130 may have a thickness of less than 0.005 inches. The material and/or thickness of the balloon may be important characteristics of the balloon impacting how the balloon acts as it is deployed and with respect to cell collection. For example, too thin of a balloon wall may result in the balloon lacking sufficient column strength (acting more compliant or elastic as desired), or too thick of a balloon wall may result in the balloon resisting everting or everting in an inconsistent manner. The thickness of the material may affect the contouring, wrinkling of the balloon surface to the extent the surface features are created or enhanced by the act of inverting, when loading the balloon in the catheter, which in turn may affect the ability to collect and retain cells. The material of the balloon may also impact whether the balloon may adhere or tend to stick to itself during eversion or after being deflated and withdrawn with the catheter.

In some embodiments, a first marker 171 may be disposed on at least a portion of catheter 126. The first marker 171 may be a preparation marker, indicating a desired position of the sheath knob 164. When the sheath knob is aligned with the first marker 171, the proximal end of the sheath 162 may be a reference point for the medical professional for balloon extension during preparation and initial cannulation of the balloon 130 into the Fallopian tube. In embodiments, at least a portion of the catheter 126, e.g., a proximal portion connected to the transparent portion 167, may be formed of a metal such as stainless steel, or other materials such as composites, or polymers, or combinations thereof. The first marker 171 may indicate to a user an appropriate location of male luer lock fitting, or sheath knob, 164 with respect to the balloon 130 within the sheath 162, so that the sheath 162 may be extended distally an initial length as a preparation step to cover, for example, approximately 10 to 20 mm length of everted balloon 130 that is used to access the proximal os before the balloon is completely everted.

When in position at the proximal os, the sheath may be pulled back from the first marker 171 to the original position, exposing the partially everted balloon tip for accessing and placement in the Fallopian tube. In embodiments, the sheath 162 may be extendable along a longitudinal axis to a point beyond the distal end of the catheter 126. When the sheath 162 is extended distally of the catheter 126, a distal tip of the sheath 162 may be an indicator for balloon advancement. The first marker 171 may include a score line, a coating substance, or a selectively oxidized region. In some embodiments, the first marker 171 may be an opaque band of material (e.g., including but not limited to polymer, or metal, or combinations thereof) attachable to at least a portion of the catheter 126 (e.g., metal portion, or hypotube 138) using, for example, an adhesive, bonding, or welding process. Such a preparation marker may allow the medical professional to know how far to deploy the balloon 130 in the initial preparation step, thereby improving the ease of use of the device by eliminating the need for an outside measuring tool and improving the safety of the procedure by eliminating any guesswork or eyeballing on the part of the user.

In some embodiments markers may be incrementally spaced apart in known predetermined distances from each other such that a medical professional may use the markers as a visual counter or measuring device to verify an approximate length of balloon that has been everted. It is appreciated that any inner cannula or catheter described herein may include indicia as described for assistance in navigating patient anatomy.

In some embodiments, a second marker 173 may be disposed on the catheter 126, e.g., a metal portion 138, to indicate a desired location of sheath knob 164 to confirm that the sheath 162 covers the deployed everting portion (balloon, suture, etc.) during device removal into the hysteroscope 20. For example, the second marker 173 may be a retraction marker. This may allow the user to visualize and confirm that the balloon 130 is fully protected by the sheath 162 during the removal process to avoid loss of cells collected on the balloon and/or extended portion. When the hysteroscopic view is obscured, for example, by blood or tissue in the distension fluid, additional user visualization by the second marker 173 may be advantageous. The second marker 173 may be formed by the same techniques used to form the first marker 171. The second marker 173 may also be included on any inner cannula or catheter described herein.

In some embodiments, a portion 167 of the catheter 126 and/or distal portion of sheath 162 may have a transparent section along its length or a portion that is translucent, optically transparent, or a combination thereof under use conditions. According to embodiments of the present disclosure, the tube or catheter 126 may include at least one visual marker. In other embodiments, the visual marker on the catheter 126 may comprise a third marker 179 disposed on the catheter 126. The third marker 179 may be located near or at the distal end of the catheter 126 shaft where the balloon 130 is connected to the catheter 126. In some embodiments, the third marker 179 may be radio opaque. The third marker 179 may visually indicate to a user the end of the catheter 126 shaft, thereby improving control of the catheter 126. The ability to visualize the end of the catheter 126 may be desirable during cannulation, when the balloon 130 is advanced beyond sheath 162 into the Fallopian tube. The third marker 179 may allow a user to visualize the distal end of the catheter 126 as the cannulation step progresses. The user may be able to see when the cannulation step is complete, e.g., when the third marker 179 aligns with the end of the sheath 162 at the os, thereby improving ease of use. The third marker 179 may be formed by the same techniques used to form the first marker 171 and/or the second marker 173. The third marker 179 may be provided in an easy to see color, for example black or blue.

In some embodiments, a string, braid, and/or suture 121 may be extendable distally of the balloon 130 as the balloon 130 everts in the form of an extendable portion of the balloon 130. In some embodiments, the string or suture may be attached to the distal end of the push rod or to the balloon tip, by bonding or adhesive, e.g., at reference numeral 118. In an inverted position of the balloon 130, the string, braid, and/or suture 121 may be positioned internal to the balloon 130, e.g., within the tube of the catheter 126 as shown in FIG. 23A. Upon eversion of the balloon 130, e.g., by actuation of the push rod, the string, braid, and/or suture may extend to a position that becomes the exterior to the balloon, either extending distally from the distal tip of the balloon 130, or extending proximally from the balloon tip alongside the exterior of the balloon.

Figure 11C:
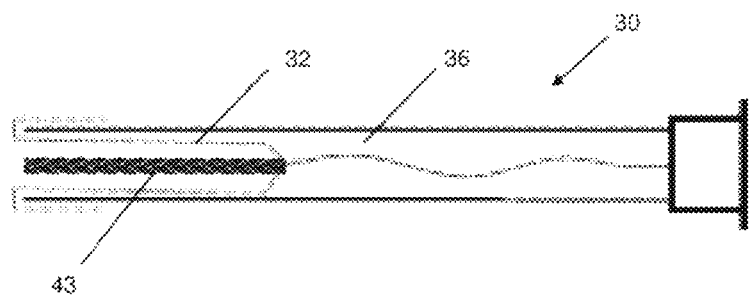
FIGS. 11C-11D illustrate cross-sectional views of an exemplary embodiment of an everting balloon catheter in accordance with the present disclosure.
Figure 11D:
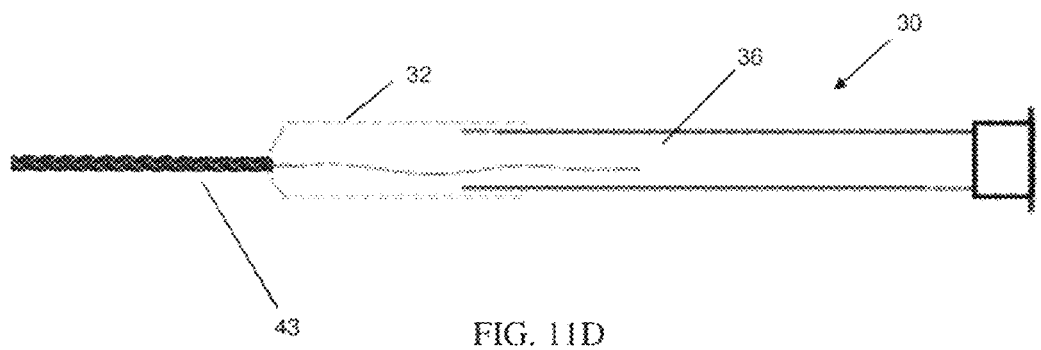
Figure 34A:
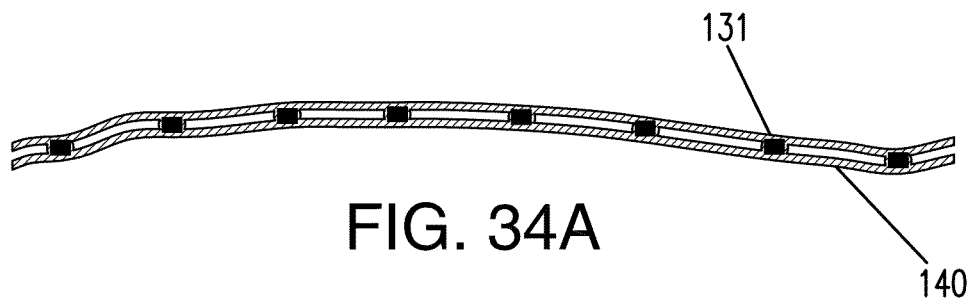
FIG. 34A illustrates a side perspective view of an exemplary embodiment of a string filament with a series of printed indicia in accordance with the present disclosure.

In some embodiments, at least a portion of the string, braid, and/or suture 121, e.g., as indicated by reference numeral 43 in FIGS. 11C-11D, may be braided. The braided string or suture 43, 121 may comprise one or more filaments. The string or suture 43, 121 may be extendable when the balloon 32, 130 is everted. In some embodiments, the string or suture 43, 121 may be a plurality of braids. In some embodiments, the string or suture 43, 121 may be formed of one or more colors, e.g., to improve visualization for the medical professional to confirm that the balloon is everting properly (see FIGS. 11E-11F). For example, the colors may be visualized through the scope as the balloon is everted and the string or suture 43, 121 is pushed out with balloon. Since the balloon 32, 130 is everting, the string or suture 43, 121 within the interior of the balloon 32, 130 may advance out of the balloon at approximately twice the distance as the balloon everts (e.g., as the balloon everts 1 mm, approximately 2 mm of string or suture is exposed beyond the distal end of the inner cannula/tube. The colors may determine positioning of the suture or string 43, 121 in the Fallopian tube for sample collection. In some embodiments, the string or suture 43, 121 may include one or more regions having printed indicia, or color variations along the length thereof, or combinations thereof. In some embodiments, the string or suture 43, 121 may include one more knots along its length in predetermined spaced known increments to provide further visual or tactile feedback to the medical professional (see FIGS. 34A-34B). The colors and/or knots may be placed at incremental distances from each other, so that a count of the colors or knots may be translated to an approximate amount of distance/length that the suture or string 43, 121 (and to some extent the length of the balloon 130) has been everted.

In some embodiments, the balloon material may be treated to change the surface properties of an exterior surface of the balloon 130. Processes such as plasma or corona treatment may increase surface receptiveness to various substances that illustratively include subject cells, inks, coatings, adhesives, laminates, and paints, or combinations thereof. Surface treatment may enhance wettability creating a surface with hydrophilic properties, or discourage wetting creating a surface with hydrophobic properties. Surface treatment may be used to improve the adhesion properties of the balloon surface, to create a surface in which cells are more likely to adhere compared to an untreated surface.

Surface treatments may also be used to prepare the balloon surface for printing indicia on the surface, e.g., including PAD printing. PAD printing (also called tampography) is a printing process that may transfer a 2-D image onto a 3-D object. Indicia printed on the balloon surface may serve as preparation markers for the user. These preparation markers may allow the user to know the length of the balloon 130 prior to deployment of the balloon 130, thereby improving the ease of use of the device by eliminating the need for an outside measuring tool and improving the safety of the procedure by eliminating any guesswork or eyeballing on the part of the user.

In addition to marking for visualization purposes, the balloon 130 may also be treated with a process that increases surface area such as the application of a nanofiber or micropillar surface (e.g., including but not limited to ULTRA-WEB® from Corning), which may improve cell collection yield and/or retention compared to a balloon with little or no surface treatment. The suture or string 121 may include similar surface treatment features as a way to enhance cell collection and retention.

In various embodiments, the balloon 130 may be formed of a material such that the balloon 130 is capable of moving between the inverted and everted positions without excessive deployment pressures, yet rigid enough so that the balloon does not excessively radially expand during eversion. The material may also allow for wrinkles, overlapping material, or micro ridges, or a combination thereof to be formed on the balloon surface during manufacturing and/or assembly, for example by polymer deformation. Such wrinkles, overlapping material, or micro-ridges may be created on a normally smooth (contourless) balloon surface material, or may enhance a balloon surface material that already includes one or more surface features. The wrinkles, overlapping material, or micro ridges formed in the balloon material may remain during balloon eversion and/or inversion, e.g., the balloon surface may be plastically deformed. Wrinkles, overlapping material, and/or micro ridges may improve cell collection of the balloon 130. For example, cells may be removed from the Fallopian tube during balloon eversion and/or may be captured within the wrinkles as the balloon 130, so that when the balloon 130 is retracted into the sheath 162 and the catheter 126 is removed with the scope, cells may be retained within the wrinkles of the balloon 130. Relieving pressure in the balloon, to deflate or partially deflate the balloon, prior to retraction, may act to increase or reform wrinkling on the balloon surface and further improve cell collection and/or retention. In some embodiments, the surface of the balloon 130 may be roughened, or otherwise adjusted, to increase a surface area. According to various embodiments, the balloon may be made of polyethylene terephthalate (PET), polyethylene, nylon, a fluoropolymer, or a perfluoropolymer, or other similar suitable material.

In some embodiments, a surface area of the balloon 130, e.g., the surface for contacting the inner surface of the body lumen (Fallopian tube) may include additional surface features. In some embodiments, a balloon surface that is relatively smooth because of the material characteristics may be modified to include wrinkling and added surface area, e.g., by processes employed during manufacture or packaging that impart surface features to the balloon surface that are retained during use of the device. In other embodiments, a balloon material surface that is maintained relatively free of any contouring, may still be able to collect and retain cells just through the mechanism of everting and engaging the tissue lumen with the balloon and then (optionally deflating and) retracting the balloon along the tissue wall, as described above. In some embodiments, a surface of the balloon 130 may be embossed to impart micro ridges having peak-to-valley heights of from approximately 0.1 to 500 microns through a variety of conventional techniques that illustratively include plate-to-plate, roll-to-plate and roll-to-roll. In some embodiments, the peaks and valleys may be configured to be large enough to provide additional surface area but small enough to minimize the potential of peaks and valleys locking together. For example, peaks and valleys in the balloon surface area may interlock during inversion/eversion such that balloon movement may be impeded. It may therefore be advantageous to configure the peaks and valleys to have a profile to minimize potential interlock.

In some embodiments, a polymer surface of the balloon 130 may be etched. Etching may be accomplished by a variety of conventional techniques including but not limited to solvent, chemical, laser, or plasma exposure. Etching may be advantageous to increase a surface area without incurring the stressing on the balloon of having embossing tool contact. This feature may improve cell collection of the balloon by increasing surface area and creating micro-edges that are normal to the axis of the balloon as it is removed. In some embodiments, as above, polymers having low surface energies and/or having a limited ability to crinkle/wrinkle at any balloon thickness upon embossing and/or etching are nonetheless operative herein for cell biopsy as the opposing contacting surfaces have sufficient glide to allow the balloon to evert smoothly, while having enough surface area to dislodge and retain cells. Low surface energy polymers in embossed or etched form may include fluoropolymers, perfluoropolymers, polyalkylenes, polypyromellitimide (Kapton H), or polystyrene, or combinations thereof.

In some embodiments, etching or embossing may be formed on a balloon surface in concentrated portions of the balloon, e.g., as indicia. For example, balloon markings may provide a visual indication for the medical professional to determine an extension of the balloon into the Fallopian tube. Concentrated etchings and/or embossing may be visible by the medical professional, e.g., potentially eliminating a need for a separately attached marker or other indicia. A marker formed as a portion of the balloon may be advantageous to minimize and/or avoid potential detachment.

The balloon 130 may be translucent, optically transparent, or a combination thereof. In some embodiments, the balloon 130 may be at least partially opaque to enhance visibility during use. In some embodiments an opaque fluid may be mixed in the inflation fluid to control color of the balloon and to further enhance visibility of the balloon. The amount of the opaque fluid added to the inflation fluid may control the level of translucence or opacity of the balloon. In some embodiments, the fluid may be rendered opaque or otherwise detectable through the inclusion of colloidal or suspended particulate or microbubbles released within the fluid. Colloidal or suspended particulate operative herein include without limitation, polymethylmethacrylate, mica, barium sulfate, starch, and combinations thereof.

The length of the fully everted balloon 130 may extend to approximately 7-12 cm within the lumen (e.g., Fallopian tube), such that when fully everted, the balloon 130 may extend within the patient's Fallopian tube, following the successful advancement of at least a portion of length of everted balloon through the UTJ. Eversion of the balloon 130 may be performed in a controlled manner, e.g., by advancing a push rod 134 through a fluid tight seal 135, at the proximal end of the catheter 126. As described above, at least a portion 167 of the catheter 126 may be transparent or translucent, so that movement of the balloon 130 may be viewable through the hysteroscope through which the catheter 126 is inserted, thereby providing the user with a direct view of the insertion procedure. The catheter 126 may be constructed of polymers such as Nylon, polyether block amide, polyurethane, PET (polyethylene terephthalate), polyethylene, or polyvinyl chloride (PVC), with or without polymer or metal coil or braid reinforcement, or combinations thereof.

In some embodiments, the transparent or translucent portion 167 of the catheter 126 may be at least approximately 1 cm in length for visualization of the balloon deployment through the hysteroscope view. Providing a transparent or translucent portion 167 that is of an adequate length may ensure visualization of the balloon deployment while providing sufficient catheter column strength for Fallopian tube cannulation. In embodiments, the transparent portion 167 of the catheter 126 may have a length relative to an opaque portion, e.g., a metal hypotube portion 138, to balance desired column strength and support to the catheter 126 with visualization at the distal end. In some embodiments, the transparent portion 167 may extend to a proximal end of the device, within the metal portion 138. It is understood that materials used to form the transparent portion 167 of the catheter 126 may have lower column strength than a metal hypotube portion 138. This balance may improve ease of use (e.g., by visualization of the distal end) and control of the device (e.g., by having sufficient stiffness to enable placement of the device at the ostium of the Fallopian tube and maintain position throughout the procedure).

In some embodiments, a balloon 130, when everted at least partially out of the catheter 126 or cannula, may not remain straight. Rather, the balloon 130 may assume an undesired curved configuration, either a single "C" curve, or an "S" curve, that may be difficult to use to cannulate the proximal os of the Fallopian tube, and to advance the balloon through the UTJ. The extended length of everted balloon 130 may be straightened out or maintained straight by use of an outer sheath 162 that lies coaxial about the exterior of catheter 126 or cannula, and may assist in providing column strength and cover of the partially everted balloon tip. At least a portion of sheath 162 and/or catheter 126 may be transparent 167, e.g., 167 of FIG. 23A, so that movement of the balloon 130 may be viewable through the hysteroscope through which the catheter is inserted, thereby providing a user with a direct view of the insertion process. Similar to catheter 126, the sheath 162 may be constructed of polymers such as Nylon, polyether block amide, polyurethane, PET (polyethylene terephthalate), polyethylene, or polyvinyl chloride (PVC), with or without polymer or metal coil or braid reinforcement, or combinations thereof. The sheath may be alignable with respect to the catheter and/or the balloon, thereby providing column strength to the balloon. In response to cannulation of the balloon through the UTJ into the Fallopian tube, the sheath may support the balloon from outside of the proximal to minimize and/or prevent collapse as the balloon is further everted after navigating the UTJ. The sheath 162 may also protect the sample (e.g., cells) collected on the balloon and/or extended portion. For example, the sheath 162 may protect the balloon in an everted position after contacting an inner surface of the Fallopian tube. In some embodiments, the sheath 162 and balloon with or without extended portion may be retracted coaxially with the inner lumen of the sheath to extend the sheath over the everted balloon, and extended portion, if included, subsequent to cell collection. In some embodiments, the sheath 162 may remain stationary relative to the balloon 130 and/or the catheter 126, so that the balloon 130 is received in the sheath 162 subsequent to cell collection. As the balloon 130 is withdrawn into the sheath and removed from the patient, the sheath may protect the cells to minimize and/or prevent loss of the sample collection by providing a barrier from distention fluid in the uterus or irrigation fluid in the Fallopian tube or uterus. For example, the balloon subsequent to cell collection may otherwise be exposed to environmental conditions that may render the sample collection unusable, and/or otherwise wash the cells from the balloon and extended portion.

Figure 35:
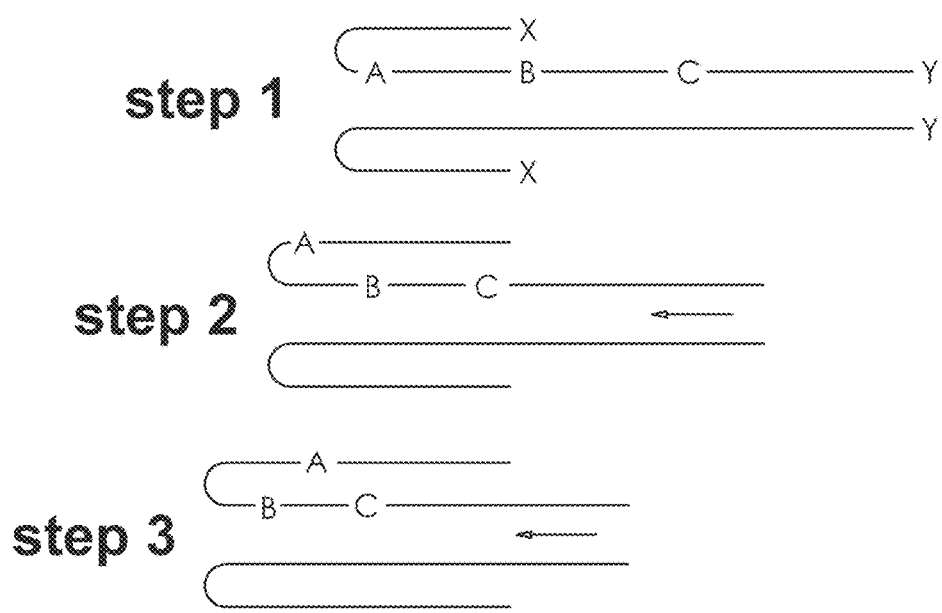
FIG. 35 illustrates an eversion of an exemplary embodiment of a balloon in accordance with the present disclosure.

FIG. 35 illustrates an exemplary embodiment of a linear eversion of a balloon 130 in accordance with the present disclosure. In embodiments, one end of the balloon may be fixed to inner cannula/tube at point X (e.g., reference numeral 117 as illustrated in FIG. 23A) and the other end of the balloon may be movable at point Y (e.g., reference numeral 118 as illustrated in FIG. 23A). The balloon 130 may evert from the position shown in Step 1 to the position shown in Step 2 to the position shown in Step 3. In the eversion process, points A, B, and C move towards the left side of the diagram, e.g., extend distal of the distal end of the device 160. As the balloon 130 unrolls/everts at/toward the left side of the diagram, point A may move from the inside surface of the balloon to the outside surface. In practice, the balloon 130 that has been partially, or initially, everted during the preparation step may be advanced further into the proximal end of the Fallopian tube. Further eversion (extension) of the balloon (in total up to the full length of the Fallopian tube, approximately 7-12 cm) may be accomplished by further rotation of a drive wheel 204 (see FIG. 25). The balloon 130 may then be deflated by relieving pressure in the inflation device. The balloon 130 may then be retracted from the Fallopian tube. Because the Fallopian tube is a potential space, the Fallopian tube tissue may tend to collapse around the balloon. Because the balloon fills the Fallopian tube, the balloon surface area may be substantially equivalent to the surface area inside the Fallopian tube. This surface area may optimize tissue collection from the inside of the Fallopian tube. While deflation of the balloon may be desirable prior to retraction, it may be possible in some embodiments to retract a balloon/extended portion from a Fallopian tube without first deflating the balloon and still retaining cells collected thereon. For example, the balloon 130 in an inflated and/or a deflated state may be retracted within the sheath 162 while retaining a sufficient amount of cells on the surface of the balloon 130 for testing. Alternatively, the balloon may be repeatedly inflated and deflated while extended in the Fallopian tube, so that each time the balloon contacts Fallopian tube walls, more cells may be collected and/or retained by the balloon.

As mentioned, to further aid tissue collection, wrinkles or other surface features may be added to the surface of the balloon. Wrinkles may form as the balloon deflates to create multiple edges and/or overlapping material, to aid in cell collection. Edges may work in a manner similar to the edges of a curette or edges of jaws in a biopsy forceps. Similar to these features on other collection devices, edges formed by the wrinkled balloon may focus a contact force on the anatomical wall in order to collect cells.

The balloon deployment device in accordance with the present disclosure may then be removed from the working channel of the hysteroscope and from the patient. Once the device is removed from the patient, cells may be removed from the balloon by dipping the balloon and/or the extending portion (if used) into a cytopreservative and stirring in order to agitate the cells. Alternatively, balloon, extending portion, and/or sheath may be cut off and placed into a cytological preservative. In some embodiments a sheath may be extendable and deployable over the balloon as the balloon is deflated and removed to protect tissue samples collected on the balloon surface.

Figure 24:
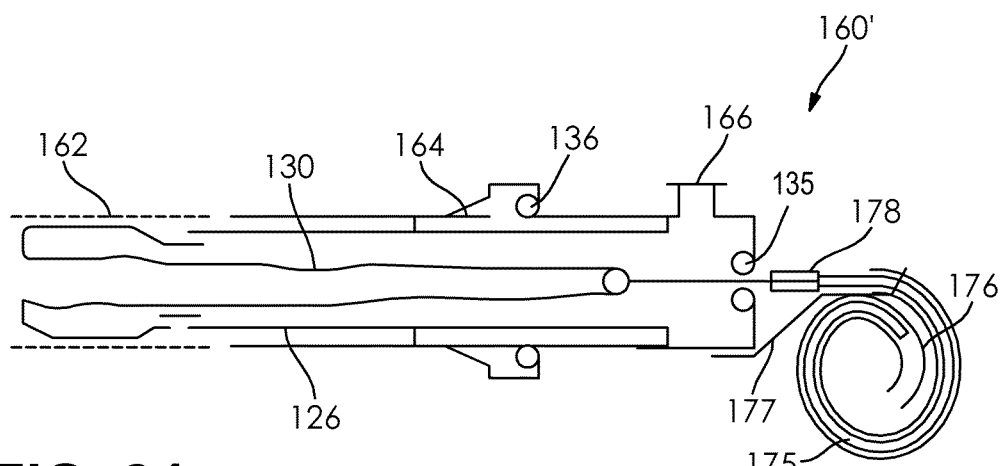
FIG. 24 illustrates a cross-sectional side view of an exemplary embodiment of a balloon tip catheter in accordance with the present disclosure.

FIG. 24 illustrates a cross-sectional side view of a balloon tip catheter 160' including a superelastic push rod 175 and spiral carrier 176. The spiral carrier may minimize and/or eliminate the need to extend the push rod backwards, e.g., outside of a handle, for the full length of the push rod in accordance with embodiments of the disclosure. The push rod 175 may be constructed of a superelastic material such as Nitinol (nickel-titanium compound) wire. At least a portion of a length of push rod 175 may be coiled into a spiraling tubular carrier 176, which may be made of polyethylene or polytetrafluoroethylene (Teflon). The outer spiral diameter of the carrier may be approximately 8 cm, rendering the proximal operating length of the catheter handle much more compact. The spiral carrier 176 may be attached to a proximal seal 135 on the catheter by a flexible strap 177. In some embodiments, the flexible strap 177 may be constructed of polymer or silicone rubber material. In some embodiments the push rod 175 may have a diameter of approximately 0.025", or some other thin diameter, which may be disadvantageous for purposes of gripping the wire and push it forward through the seal 135. A flexible grip 178 may be included that slides freely on the push rod 175, but upon compression between the thumb and forefinger, may provide a grip for push rod 175 advancement. The flexible grip 178 may be an elliptical cross-section frame that may be made of polyvinyl chloride, silicone rubber, or combinations thereof, or similar flexible compound. In some embodiments, the flexible grip may have inner dimensions of approximately 2 cm in length, 1 cm in width, and 3 mm in height, and may have a wall thickness of approximately 2 mm. Holes in the proximal and distal faces of the grip may be a slip fit with the push rod 175.

Figure 25:
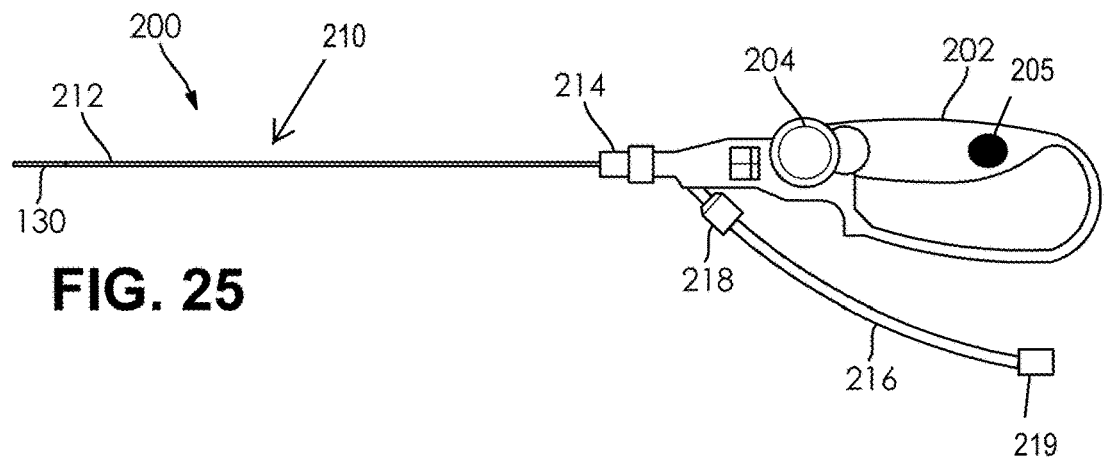
FIG. 25 illustrates a side view of an exemplary embodiment of a balloon tip catheter in accordance with the present disclosure.

FIG. 25 illustrates an exemplary embodiment of a balloon tip catheter 200 configured with handle 202. In embodiments, the handle 202 may be included in the device 160 as illustrated in FIG. 23A. The handle 202 may house a gear mechanism 220 (see FIGS. 26A-26B), also referred to herein as an actuator. The handle 202 may be in mechanical communication with a push wire 134, 206 and may control actuation of the push wire 134, 206, which in turn may control actuation of the balloon 130 between an inverted position and an everted position. Handle 202 may include a drive wheel 204 for advancement and retraction of the push wire 134, 206, in which the balloon 130 may evert linearly (e.g., gradually unfold or unroll from the inside out.). The drive wheel 204 may be made of polymer material including but not limited to ABS. The outer edge of the drive wheel 204 may include notches, or a knurl pattern, to facilitate gripping the wheel during operation of the catheter 200. The outer edge of the drive wheel 204 may include multiple features shaped like arrow heads that facilitate gripping and/or may indicate correct direction of travel of the drive wheel. A top surface of the drive wheel 204 may have an arrow molded into it for indication of a correct direction in which to turn in order to evert the balloon. The opposite side of the drive wheel 204 may include a square boss 222 insertable into a drive gear 224. In some embodiments, the gear mechanism 220 may include a step-down gearing that provides a reduced amount of extension of the push wire 134, 206 relative to a given rotational distance travelled by the drive wheel 204 (i.e., the drive wheel 204 must be turned more of a distance to accomplish the same extended length of balloon everted, than if step-down gears were not included or a different ratio of step-down was included). The resultant effect may be to have a finer control over the eversion of the balloon 130 as the drive wheel 204 is turned.

The catheter 200 may retain the balloon 130 in a shaft 210 (which may at least partially be formed of a stainless steel tube and/or a Nylon tube), a sheath 212, and/or a sheath knob 214. For balloon advancement, the balloon 130 and shaft 210 may be pressurized with an inflation device (such as inflation device 172 of FIG. 23C) that is attachable to an extension tube 168, 216, or to luer 218, of the handle 202 (see FIGS. 26A-26B). Once the catheter device 200 is pressurized, a user may rotate the drive wheel 204 causing a push wire 134, 206 to advance. Although in some embodiments, the balloon 130 may evert under pressurization without a drive wheel advancement of the push wire 134, 206, it is understood that the drive wheel may allow for smooth, slow, controlled advancement of the balloon, thereby minimizing or avoiding potential perforation of the Fallopian tube. The sheath knob 214 may allow the sheath 162, 212 to be used as an introducer as the sheath 162, 212 locks onto the body of the catheter 126, 210. The sheath knob 214 may be compliant enough to allow the user to move the sheath 162, 212 when needed, for example to the pre-extended portion of the balloon and to move the pre-extended portion of the balloon into the Fallopian tube. In embodiments, the sheath knob 214 may be tight enough such that unintended balloon or catheter movement may be minimized and/or prevented.

Figure 26B:
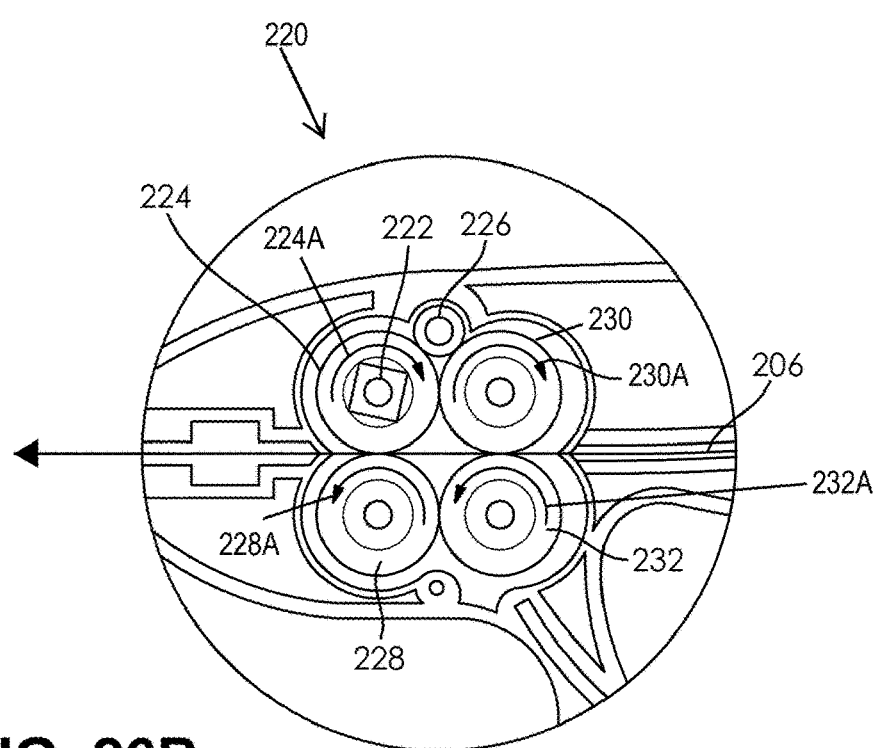
FIG. 26B is a detail view illustrating an exemplary embodiment of a gear system in the handle portion of the catheter of FIG. 26A in accordance with the present disclosure.
Figure 26A:
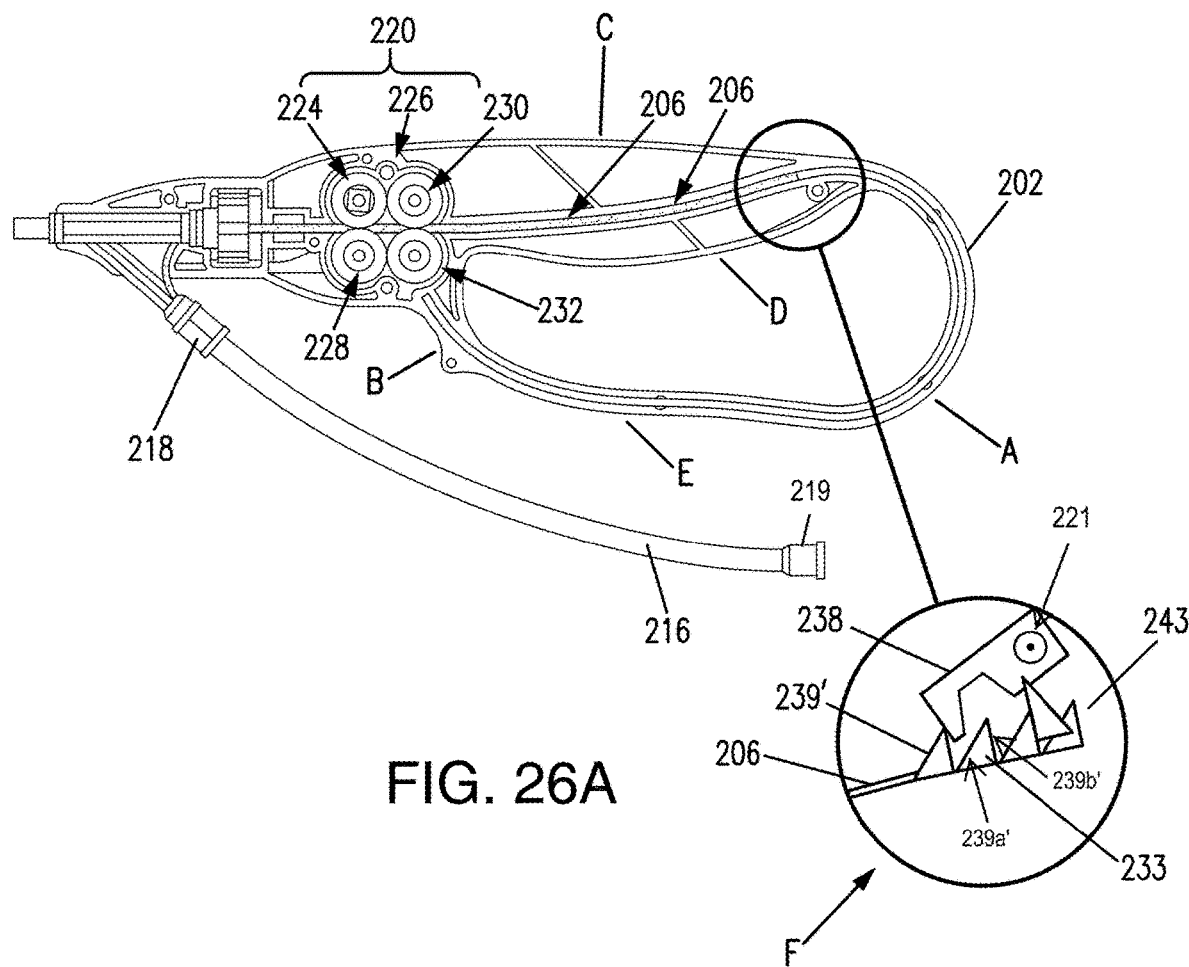
FIG. 26A illustrates a cross-sectional view of an exemplary embodiment of a handle of the catheter of FIG. 25 in accordance with the present disclosure.

FIG. 26A is a cross-sectional view of the handle portion of FIG. 25, and FIG. 26B is a detail view of an exemplary embodiment of an internal handle gear mechanism 220 in accordance with the present disclosure. The handle 202 may also have an extension tube 168, 216 that is attached to a luer 218 in the handle body, e.g., for attaching one or more additional tools or devices such as inflation device 172 (see also FIG. 23C). The gear mechanism or actuator 220 may be in mechanical communication with the push wire 134, 206, and may control actuation of the push wire 134, 206, which in turn may control actuation of the balloon 130 between the inverted position and the everted position. In some embodiments, the gear mechanism or actuator 220 may include a plurality of gears operating enmeshed to have a step-down ratio. According to various embodiments, the handle gear mechanism 220 may include a drive wheel 204, which allows controlled actuation of the gear mechanism 220 and single user operation. The loop "A" as shown in FIG. 26A may be included in the handle 202 and the feature for positioning a finger "B" may allow for a user to hold the handle 202 in more than one position and may allow for comfortable use of the device no matter the hand size of the user. For example, if the palm of the user's hand is on the top of the handle "C", the fingers of the hand may wrap around the inside of the loop "D" for a small hand, or the outside of the loop "E" for a large hand.

In some embodiments, the drive wheel 204 may have a square boss insertable into square hole 222 in the drive gear 224. The drive wheel 204, operable by a medical professional, may be rotatable so that the square boss may cause drive gear 224 to rotate. In embodiments, the drive gear 224 may be rotatable in a direction indicated by arrow 224A by the drive wheel 204 (see FIG. 26B). The drive gear 224 may engage an idler gear 226 and first gear 228, causing these gears to rotate. For example, the first gear 228 may rotate in a direction indicated by arrow 228A, which may be a direction opposite of arrow 224A. Likewise, the idler gear 226 may rotate second gear 230 in a direction indicated by arrow 230A, and third gear 232, in a direction indicated by arrow 232A in response to rotation of the second gear 230. The push wire 206 may extend between surfaces on and between each of the four gears (224, 228, 230, 232), which may each rotate as shown by arrows 224A, 228A, 230A, 232A in FIG. 26B during advancement of balloon 130 (e.g., in a distal direction) via the push wire 206. In some embodiments, gear surfaces may be formed of a material having a high coefficient of friction such as natural or silicone rubber, or polyurethane.

The balloon 130 may be advanceable until a proximal end of the push wire 134, 206 passes between the drive gear 224 and may be in mechanical communication with first gear 228. Once the push wire 134, 206 has passed beyond the gear mechanism 220, further rotation of the drive wheel 204 may not advance the balloon 130 further. The absence of the push wire 134, 206 in the gears 224, 228, 230, 232 may be felt by the user as a tactile indicator of the balloon 130 being fully everted. The gear mechanism 220 by being in mechanical communication with the push wire 206 may allow for fine, precise, and controllable movement for the deployment and/or retraction of the balloon 130 through eversion and inversion, respectively. As mentioned, the drive wheel may provide for slow and uniform movement for minimizing a potential of perforating the Fallopian tube, or inability to navigate the Fallopian tube. The gear mechanism 220 may be a 4 to 1 gear ratio, or a 2 to 1 gear ratio, and it is understood that any other gear ratios may be used to provide control of the advancement of the balloon. A gear ratio may be configured to provide slow gear rotation. This may ensure that the deployment speed of the balloon is controlled (e.g., slow and uniform) across users, thereby increasing safety by reducing the risk of adverse events such as perforation.

Figure 26C:
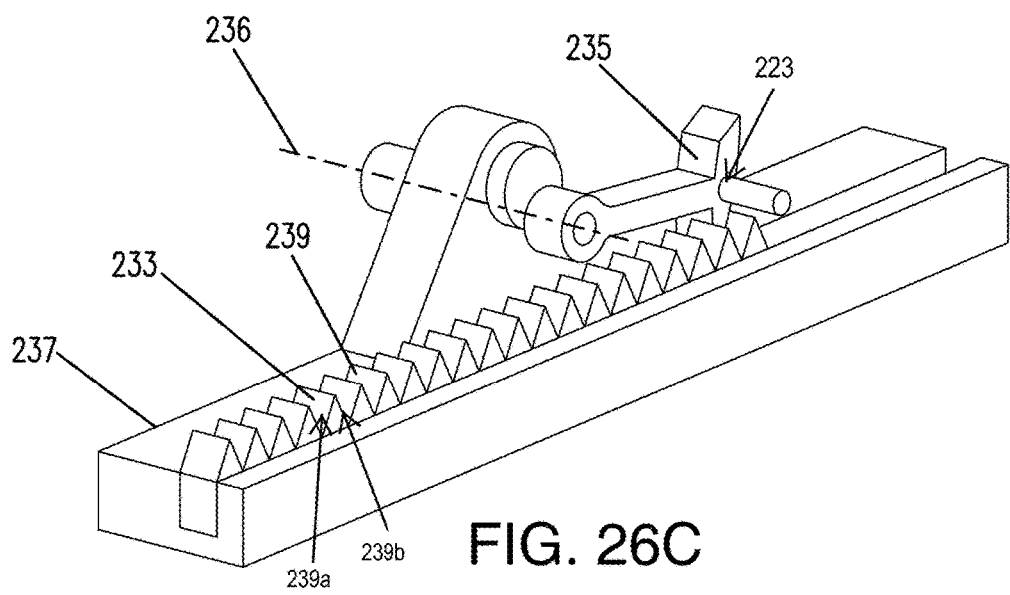
FIG. 26C illustrates a perspective view of an exemplary embodiment of a linear rack ratcheting assembly in accordance with the present disclosure.

In some embodiments, to provide feedback to the physician regarding the end of balloon deployment, the internal handle gear mechanism 220 or actuator may include a limit mechanism on the gears for limiting the advancement of the push wire and/or a unidirectional balloon movement. In some embodiments, the limit mechanism may include at least one of a hard stop, a gear jam, a rack and pawl gear, a linear gear, or a drop key-click in mechanism. At a predefined maximum extension, a pawl 242 may engage with one or more gears (e.g., gears 224, 228, 230, 232) as shown in FIG. 26E, to form a gear jam. The pawl 242 may be activated to stop further advancement of the balloon 130. In embodiments, the pawl 242 may be any mechanism configured to engage with one or more gears. For example, at a predefined push wire extension, the pawl 242 may rotate around a pivot point to engage with one or more gears, causing a jam and preventing further rotation. Alternatively, a rack and pawl gear, a linear gear, or a drop key-click-in mechanism (FIG. 26D) may be employed to stop advancement of the balloon and in some embodiments may be disposed in the handle (see FIG. 26A, detail "F"). Referring to FIG. 26C, an exemplary ratchet mechanism for linear motion is shown. Ratchets are mechanisms that serve to limit motion to only one direction. A ratchet may have three main parts: a linear gear rack 233, a pawl 235 (e.g., a "click"), and a base or mount 237. The edges on one side of the teeth 239, 239' on the linear rack may have a steep slope while the other edges of the rack's teeth may have a moderate or gradual slope. For example, edges on one side of the teeth 239, 239' may be steeper than edges on another side of the teeth 239, 239'. In some embodiments, a steeper slope may have an angle of approximately 60°-90°, e.g., as indicated at 239a, 239a', and a more moderate slope may have an angle of approximately 10°-50°, e.g., as indicated at 239b, 239b'. The pawl 235 may contact the linear gear rack 233. When the linear rack is linearly moved in a first direction, the pawl 235 may slide over the teeth 239 without restricting the natural motion of the device. When the direction of motion is reversed to a second direction, the pawl 235 may contact the steep slope on the gear tooth 239 to impede motion. The pawl 235 may be biased downward by a spring into the linear gear rack 233. In some embodiments, a spring, e.g., a torsional spring, may be disposed at a pivot point 236, e.g., at a first end of pawl 235, for pivotable rotation of the second end of the pawl 235. In some embodiments, a spring, e.g., a linear spring, may be disposed at a second end of the pawl 235, as indicated by reference numeral 223, to bias the pawl 235 towards the gear teeth 239. The linear gear rack 233 and pawl 235 may be typically mounted in a fixed relationship to one another on a mount 237, with the rack sliding in relation to the mount and the pawl 235 having a pivot connection to the mount. In some embodiments, the device may include a manual knob or push button switch to overcome the spring bias on the pawl 235 to allow for the lifting of the pawl 235 from the set of teeth on the linear gear.

A limit may be set on the ratcheting action of the linear gear rack 233 in the gear mechanism 220 of FIGS. 26A-26B to set a limit on the advancement of the push wire 206, e.g., as shown at "F". During advancement of the push wire 206, a pawl 238 may be biased toward from linear gear rack 233 as shown in detail "F" of FIG. 26A. In some embodiments, the pawl 238 may be pivotal about a point, as indicated by reference numeral 221. Linear gear rack 233 may be directly attached to the end of the push wire 206 away from the balloon 130 in the handle 202. Advancement of the push wire 206 may be automatically stopped when pawl 238 meets stop 243, which may be greater in height than teeth 239'. A manual knob or push button switch 205 as illustrated in FIG. 25 may be actuatable by a user to overcome a spring bias on the pawl 238 to allow for the lifting of the pawl 238 from the linear gear rack 233 and for retraction of the push wire 206 and the attached balloon 130. In FIG. 26D, in another embodiment different from the ratcheting action of the linear gear rack 233, the push wire 206 may be continuously and smoothly advanced and coiled around deployment wheel 245 until pawl 235 reaches and engages with detent 247 to stop further advancement of the balloon 130. In FIG. 26E, the pawl 235 may act as a gear jam when an extension limit of the balloon 130 is reached.

The sequence of steps used to enter and track through the Fallopian tube may be described with the embodiment of FIG. 23A. When it is desired to cross the UTJ with a length (e.g., approximately 15 mm) of an everted balloon 130, the outer sheath 162 may be placed in apposition with the proximal os of the Fallopian tube, without entering the proximal os. The outer sheath 162 may support the initial length of everted balloon 130 until it enters the proximal os. A portion of the balloon, e.g., a short length, of pressurized everted balloon 130 exiting the supportive outer sheath 162 may have sufficient column strength to be manually advanceable through the UTJ, whereas an unsupported length (e.g., without the sheath) of the everted balloon 130 may not contain sufficient rigidity by itself. As such, an everted/everting balloon 130 may buckle upon attempted advancement through the proximal os and UTJ without a sheath. In some embodiments, crossing the UTJ with a length of the everted balloon (e.g., 15 mm), may occur. This initial cannulation length may support keeping the Fallopian tube open even if a spasm occurs, which may occur in this area of the Fallopian tube. It is also understood that other cannulation lengths may be utilized to maintain an open Fallopian tube.

In some embodiments, the sheath 162 may be compatible with standard hysteroscopes having a working channel, e.g., 5F. A sheath 162 may be used in an exemplary system as a balance to provide a wall thickness great enough to impart sufficient column strength to the sheath and thin enough to maintain a sheath inner diameter large enough to accommodate the balloon 130. This balance may improve cell collection efficiency, e.g., by having an inner diameter sufficient to retain the balloon 130 without inadvertently removing (scraping) cells from the balloon surface. It is understood that the balloon 130 may be retained within the sheath 162 in an inflated state and/or a deflated state.

As mentioned, a male luer lock fitting, or sheath knob, 164 including a Tuohy-Borst seal 136 connector may be included at the proximal end of the sheath 162. A Tuohy-Borst adapter that includes seal 136 is a medical device used for creating seals between devices and attaching catheters to other devices. The Touhy-Borst seal 136 may be tightened to have a slip fit with the catheter or cannula holding the sheath 162 in place. The sheath knob 164 may mate with a female luer lock fitting, if present, at an instrumentation port, on the working channel of the hysteroscope 20. Referring back to FIG. 3, the male luer lock or sheath knob 164 may be connectable to the instrumentation port 23 so that the catheter 126 and/or sheath 162 may move with the hysteroscope 20. In some embodiments, the instrumentation port 23 may further include a seal for the catheter 126 to extend through. When these respective luer fittings are connected, the tip of the sheath 162 may protrude out of the distal end of the hysteroscope, e.g., approximately 2-3 cm. The sheath 162 may also protect a portion of a balloon 130 everted during device preparation (e.g., a length approximately 1.5 cm) from injury as the catheter 126 is advanced through the working channel of the hysteroscope. A stainless steel tube, e.g., hypotube 138, may be at least a portion the inner cannula 126 to provide sufficient rigidity and/or column strength to minimize or prevent kinking of the portion protruding from the proximal end of the hysteroscope working channel. In some embodiments, the hypotube 138 may be sized having approximately 0.050" OD×0.004" wall thickness for sufficient rigidity.

In some embodiments, the hypotube 138 may ensure that the handle 202 is undisturbed, or does not fall out of the working channel of the hysteroscope 20 when a medical professional releases the device during a procedure. The sheath 162 may be coaxial with the tube or catheter 126 and may be slidably adjustable to cover at least a first length of the balloon extending outward from the distal end in the everted position. The sheath 162 may form a physical barrier and may protect the balloon in at least one of the inverted position, a partially everted position, and/or a fully everted position and may serve to protect collected cells from dislodgement during transit out of the patient body.

As mentioned, at least a portion of each of the sheath 162, a portion of the tube or catheter 126, and/or the balloon 130 may be translucent, optically transparent, or a combination thereof, to facilitate visual feedback of relative positions of the aforementioned device components during deployment and retraction. It is understood that a hysteroscope 20 may be well suited for visual observation of a cell collection with the device. Translucency and/or transparency of a device component may be dependent on the observational wavelengths. By way of example thermoplastic materials can appear clear under visible light, yet are opaque to other portions of the electromagnetic spectrum.

Figure 23C:
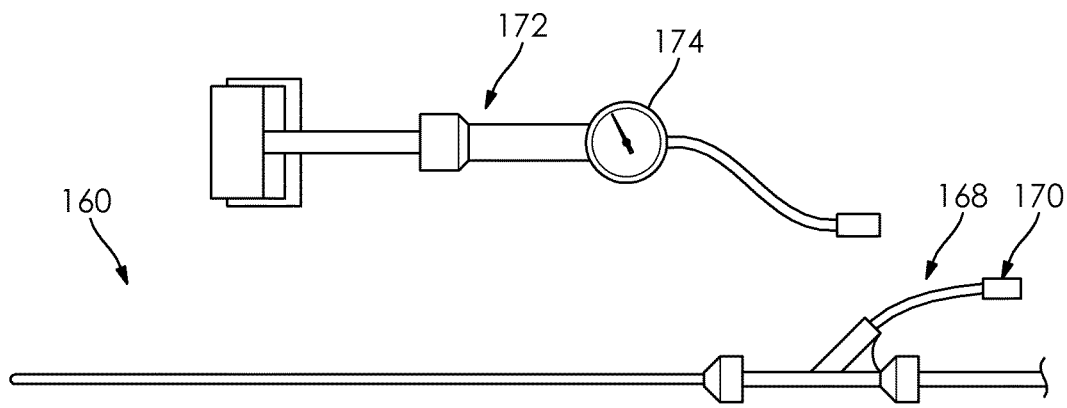
FIG. 23C illustrates the balloon tip catheter of FIG. 23A in accordance with the present disclosure.

FIG. 23C illustrates a balloon tip catheter 160 of FIG. 23A with a tubing reservoir, or extension tube 168, and inflation device 172 in accordance with an exemplary embodiment of the disclosure. It is understood that in some embodiments the extension tube 168 may be similar to extension tube 216 as shown in FIG. 26A. The extension tube 168, 216 may be configured to withstand pressurization. Pressurization of the balloon 130 by fluid injection may be performed using a syringe device, such as the exemplary inflation device 172. Rotation of a threaded plunger shaft through a releasable lock may increase and maintain pressure in the inflation device 172, while a pressure gauge 174 provided with the inflation device 172 may allow for control of input pressure. In some embodiments, the balloon tip catheter 160 may provide for a one-person operation of the device. A length of pressure tubing, or extension tube 168, 216, may be added between the inflation device 172 and the inflation port 166 on the device. The extension tube 168, 216 may be constructed of polymers such as polyurethane or polyvinyl chloride (PVC), with or without polymer or metal coil or braid reinforcement. The extension tube 168, 216 may contain an amount of intrinsic elasticity, while the everting balloon may be generally inelastic. At full pressurization of the balloon 130, the extension tube 168, 216 may impart a fluid capacitance to the system. A small volume of fluid may be containable in the everted balloon, and this volume may be further subtracted by the volume occupied by the push rod 134 (e.g., which moves into the balloon 130 as it is being everted). The resultant everted balloon volume may be small compared with the larger volume in the pressure tubing 168, which may allow the balloon 130 to evert to its full length without significant decrease in pressure, once the balloon tip catheter 160 has been pressurized.

A length of an extension tube 168, 216 may be added between the inflation device 172 and the inflation port 166 on the device in response to positioning a stopcock valve 170 in a location proximal, or away, from the device and the hysteroscope 20. For example, as shown in FIG. 25, luer 218 may connect pressure tubing 168, 216, for connection with a stopcock valve 170. In embodiments, a stopcock valve 170 may be disposed at an end of extension tube 168, 216 for connection with a luer 219 and the inflation device 172. In some embodiments, the stopcock valve 170 may be connected to the luer 218. The stopcock valve 170 may be closed following pressurization, and the inflation device 172 may be removed from the examination field, prior to insertion and eversion of the balloon 130. This one-operator procedure may be less cumbersome and more efficient during a medical procedure. It is also understood that in some embodiments, the luer 219 may be connectable to the inflation device 172 without a stopcock valve 170.

As described above with respect to FIGS. 23A-23C, the everting balloon 130 may be extendable a total distance of approximately 7 cm distal to the tip of the catheter, in order to pass through the entire length of the Fallopian tube. The everting balloon 130 may form a toroidal shape at the end 130a as it exits the catheter tip, and the everted portion may include a double walled configuration. A toroidal shape may be an atraumatic shape for minimizing or avoiding damage during extension into the Fallopian tube. Thus, for example, the push rod 134 advances forward a distance of approximately 14 cm in order to yield an everted balloon length of 7 cm. This length of push rod may initially extend backwards from the proximal end of the catheter 126, directly into the face of the operator, making its use cumbersome. The push rod may also be susceptible to contamination of the sterile device due to its length as it may extend into a physician's working space during a procedure. For example, the proximal end of the long push rod 134 may contact the physician's face or surgical mask during use. Therefore, it may be desirable to provide a push rod system that does not have to extend backwards for the full length of the push rod 134. The superelastic push rod 175 and carrier design of FIG. 24 and the balloon tip catheter 200 configured with handle 202 of FIG. 25 may contain the push rod and minimize and/or avoid the need to extend the push rod back towards the user.

Figure 27:
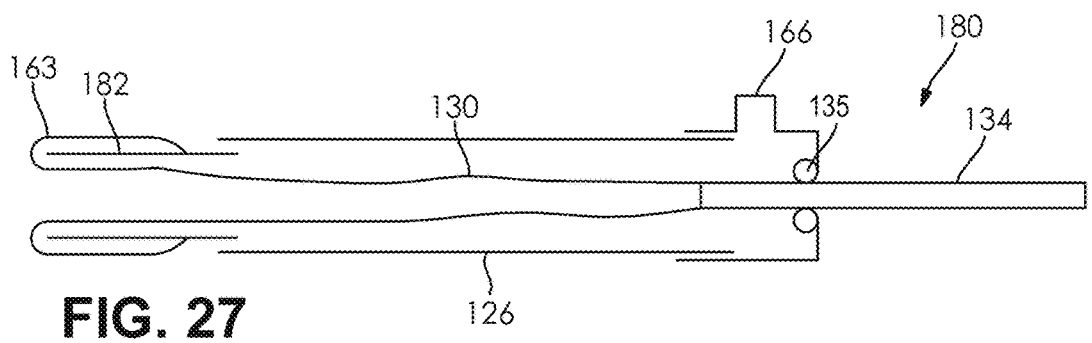
FIG. 27 illustrates a cross-sectional side view of an exemplary embodiment of a balloon tip catheter in accordance with the present disclosure.

FIG. 27 illustrates a cross-sectional side view of an exemplary everted balloon tip catheter 180 including a tube 182 having diameter smaller than the inflated diameter of the everting balloon 130 for insertion into the patient's UTJ in accordance with the present disclosure. The tube 182 may straighten a portion of the balloon tip 163. In some embodiments, the tube 182 may extend distally to the tip of the cannula. In embodiments, the tube 182 may have an approximately 0.0005"-0.001" wall thickness (e.g., being a "thin-walled" tube), and may extend approximately 1.5 cm distal to the tip of the cannula. The tube 182 may have a thickness and resiliency sufficient to support the balloon 130, to maintain a position of the balloon tip 163 (e.g., maintain a straight position). In some embodiments, the tube 182 diameter may be smaller than the balloon 130 diameter, so that the balloon 130 may retain flexibility and compressibility. This flexibility may be beneficial to allow the balloon 130 to be advanced through the UTJ. In some embodiments, the balloon 130 may include the tube 182 to support and/or straighten the balloon. In embodiments, the tube 182 may have a 0.033" OD×0.001" wall×1.5 cm long.

Figure 28:
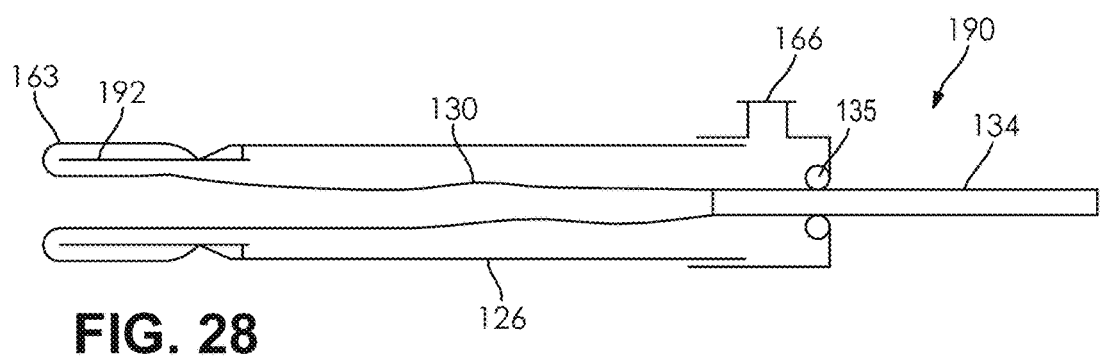
FIG. 28 illustrates a cross-sectional side view of an exemplary embodiment of a balloon tip catheter in accordance with the present disclosure.

FIG. 28 illustrates a cross-sectional side view of an everted balloon tip catheter 190 including one or more flexible polymer monofilament string and/or suture 192 as an extending portion attached to the distal end of the cannula or catheter 126. The strands 192 may extend into everting balloon tip 163, thereby supporting and keeping the tip straight for insertion into the patient's UTJ in accordance with an embodiment of the present disclosure. In some embodiments, the one or more flexible polymer monofilament string and/or suture 192 may extend into the balloon tip 163 (e.g., approximately 1.5 cm). The monofilament 192 may be formed of nylon, polypropylene, or other flexible polymer material, or combinations thereof. The monofilament strands may have a diameter of approximately 0.006"-0.012". In some embodiments, the balloon 130 may have approximately a 0.033" (0.8 mm) OD with a 0.008" diameter monofilament 192 inside an approximately 1.5 cm long everted balloon tip.

Figures 29A, 29B, 29C:
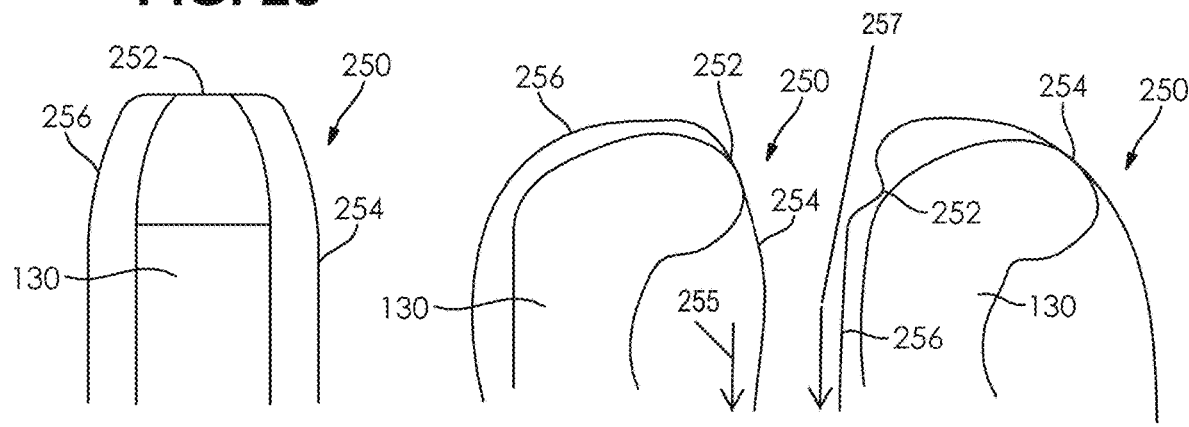
FIGS. 29A-29C are a series of side perspective views of an exemplary embodiment of a steerable balloon tip using guide wires in accordance with the present disclosure.

FIGS. 29A-29C illustrate a steerable balloon tip 252 for an everted balloon catheter 250 using guide wires in accordance with an exemplary embodiment of the present disclosure. As shown in FIG. 29A a steerable balloon tip 252 may be controllable by a right direction guide wire 254 and a left direction guide wire 256. In FIG. 29B the right guide wire 254 may be manipulated (e.g., pulled, as shown by the arrow 255) to steer the balloon tip 252 to the right. Conversely, in FIG. 29C, the left guide wire 256 may be manipulated, (e.g., pulled, as shown by the arrow 257) to steer the balloon tip 252 to the left. It is noted that additional guide wires may be included to provide movement in the Z-plane in addition to movement in the X-Y plane achieved with the pair of guide wires as shown.

Figure 30:
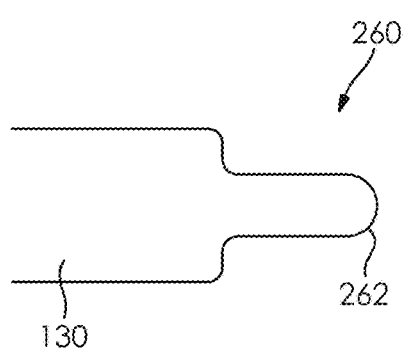
FIG. 30 illustrates a side perspective view of an exemplary embodiment of a balloon catheter and lead balloon tip in accordance with the present disclosure.

FIG. 30 illustrates a side perspective view of a balloon catheter 260 having a smaller diameter lead balloon tip 262 at the distal end of the everted balloon 130 in accordance with an exemplary embodiment of the present disclosure. The smaller diameter lead balloon tip 262 may be dimensioned so as to gradually expand the opening at the constriction of the UTJ, while being flexible with blunted edges so as not to perforate the walls at the UTJ.

Figure 31:
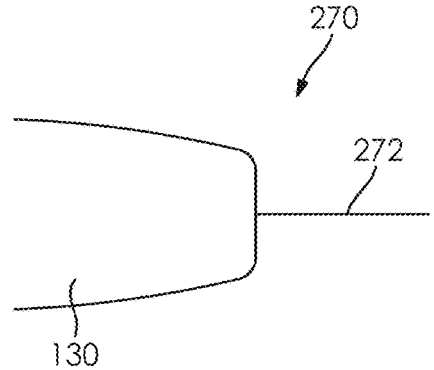
FIG. 31 illustrates a side perspective view of an exemplary embodiment of a balloon catheter with a flexible guide wire in accordance with the present disclosure.

FIG. 31 illustrates a side perspective view of a balloon catheter 270 with a flexible guide wire 272 on the tip of the balloon 30 in accordance with an exemplary embodiment of the present disclosure. The flexible guide wire may lead the balloon catheter 220 through the UTJ into the Fallopian tube.

In embodiments, a portion of the everted balloon may be treated with fluoropolymer, silicone, and like material coatings, or combinations thereof, lubricating the surface at the lead portion of the balloon catheter, which may enter the constricted portions of the Fallopian tube (e.g., the UTJ).

Figure 32:
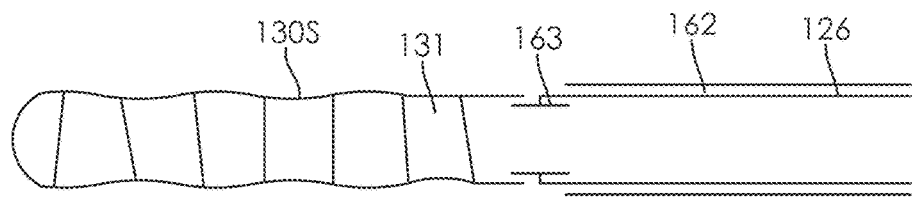
FIG. 32 illustrates an exemplary embodiment of a balloon prior to inversion of the balloon into a catheter in accordance with the present disclosure.

FIG. 32 illustrates a partial side perspective view of a striped balloon 130S prior to inversion of the striped balloon 130S into the catheter or cannula of FIG. 32 in accordance with an embodiment of the disclosure. The indicia 131 on the balloon provide a visual feedback indicator of the progress of the balloon eversion. In a specific embodiment, the indicia 131 may be approximately 1 mm wide and spaced at approximately 1 cm increments along the entire length of the balloon 130S. Alternative spacing of the strips or other visual markers on the balloon may be spaced closer together for finer positional feedback, or further apart for coarser feedback. Other visual markers of length of eversion may include sinusoidal indicia with a known length of periodicity. It is also appreciated that indicia of length may also include differently colorized segments of a known length.

Figure 33:
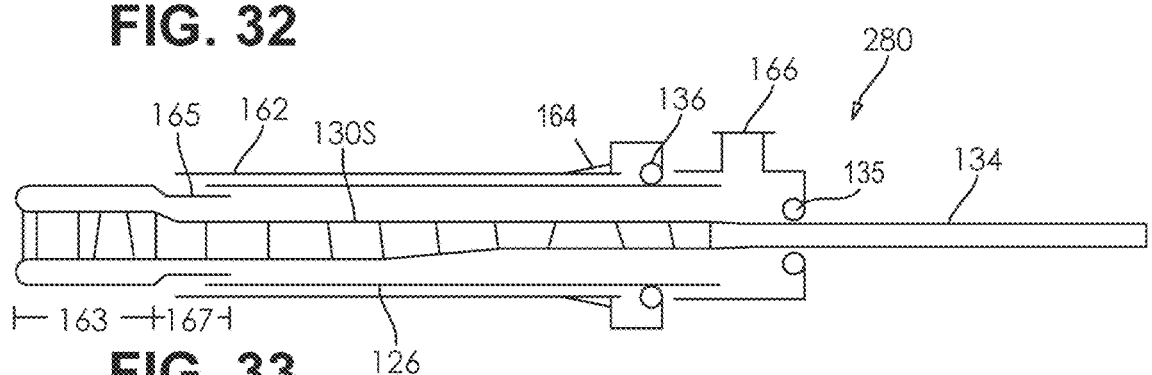
FIG. 33 illustrates a cross-sectional side view of an exemplary embodiment of a balloon tip catheter with a sheath and the balloon of FIG. 32 inverted in accordance with the present disclosure.

FIG. 33 illustrates a cross-sectional side view of a balloon tip catheter 280 configured with striped balloon 130S in accordance with an exemplary embodiment of the present disclosure. As shown in FIG. 33, the indicia 131 of the striped everting balloon 130S may be coupled with a transparent distal section 167 of the cannula or catheter 126 to provide visual feedback of balloon eversion. In some embodiments, the indicia may be pad printed or scribed with an indelible marker in a highly visible color. In some embodiments, the indicia 131 may be approximately 1 mm wide, spaced approximately in 0.5 cm increments along the entire length of the balloon. Pad printing (also called tampography) is a printing process for transferring a 2-D image onto a 3-D object. Other patterns may be used instead of, or in addition to, indicia 131 on the surface of the balloon 130S. For example, indicium 131 on the balloon 130S may be spaced apart (e.g., approximately 0.5 cm), and dots may also be added in the remaining intervals between the indicia 131. Each indicium 131 that comes into view in the transparent distal section 167 may indicate a successful eversion of a length of a balloon 130S (e.g., 0.25 cm, as the push rod is advanced approximately twice the length for a corresponding approximate length of balloon eversion (e.g., 0.5 cm). Indicia 131 of different thicknesses may be used, as well as different colored indicia, or a different number of indicia, or combinations thereof, in the same fashion described for the stripe and dot combination. In some embodiments, color coded sections may be added to the balloon 130S to indicate the extent of the balloon eversion.

Figure 34B:
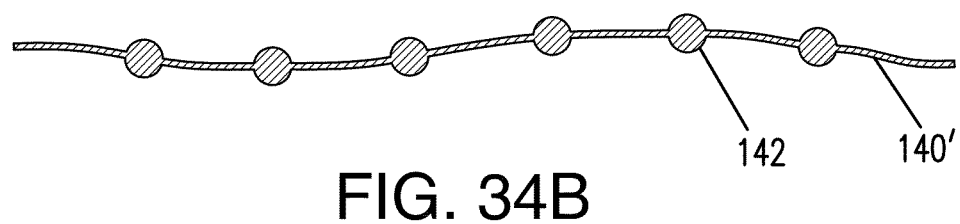
FIG. 34B illustrates a side perspective view of an exemplary embodiment of a string filament with a series of knots as indicia in accordance with the present disclosure.

Additional embodiments of feedback markers, which may be externally visible to the physician on the outside of the patient's body, for the extent of positive balloon eversion. In some embodiments, a knotted string or braided sutures as an extending portion may be adhered to the distal end of the push rod or tip of the balloon, and may be spaced in known increments to provide tactile feedback as to balloon eversion progress. The knotted string or braided sutures may allow for visualization of the forward movement of the balloon as it is everted. The knotted string or sutures may be radio opaque. The string may have color coded zones for providing visual feedback to the operator. To enhance visualization of the knotted string or braided sutures, the sutures, indicia, or color-coded zones may be provided in a highly contrasting color from the catheter and anatomy. In some embodiments, the braided surface of the sutures may assist with collection and/or retention of cells due to the texture and folds of the braid. For example, tissue and/or cells may become embedded in the texture and/or folds of the braiding. In some embodiments shown in FIG. 34A, a string 140 may be pad printed with indicia 131 in a similar manner to the balloon as noted above in FIGS. 32 and 33. FIG. 34B illustrates a string 140' with a series of knots or sutures 142. The balloon 130 may be at least partially transparent to enhance visibility of string, indicia, knots, or sutures.

In some embodiments, the string as an extending portion may be braided as shown in FIGS. 11C and 11D. The braided string, knots, or sutures may also provide an additional cell collection surface. In some embodiments, cells may be collected and retained within the braiding of the suture 43, which may be advantageous over cells collected only on a suture surface. Cells collected within the braiding of the suture 43 may be less likely to be inadvertently removed or wiped away during retraction of the suture 43 and/or balloon 32, as cells may be collected between braiding, thereby providing protection of the collected cells.

Figure 11E:
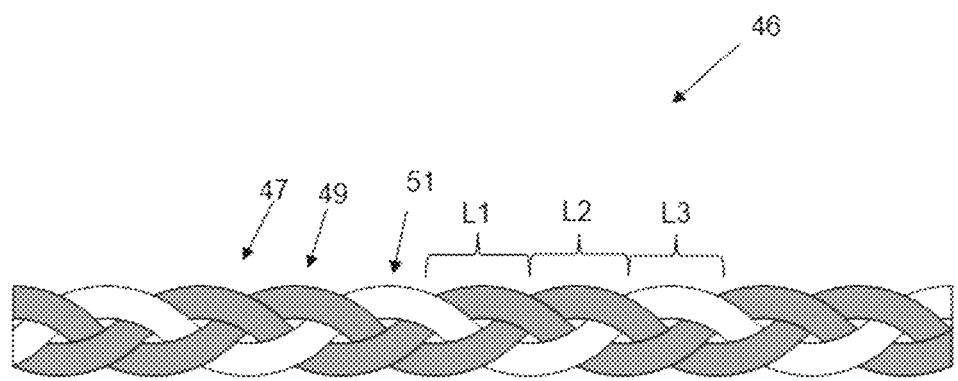
FIGS. 11E-11F illustrate cross-sectional views of an exemplary embodiment of an everting balloon catheter in accordance with the present disclosure.
Figure 11F:
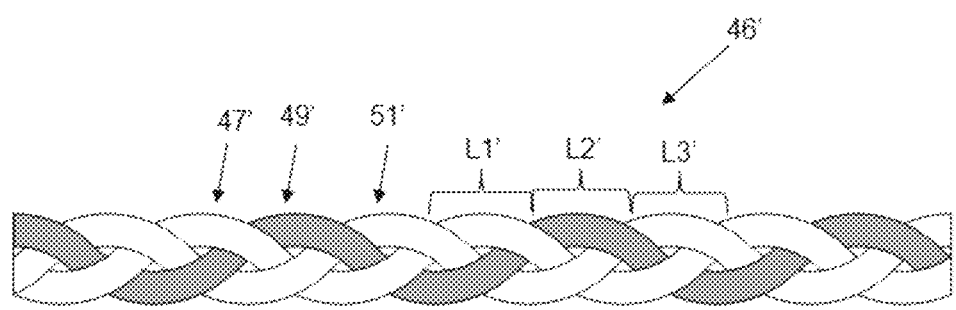

In some embodiments, different strands of the string or suture may be formed of different colors, shades, or thicknesses, relative to other strands, as shown in FIGS. 11E and 11F. For example, as shown in a three-strand suture in FIG. 11E, strands 47 and 49 of suture 46 may be a different color or darker shade as compared to strand 51. Alternatively, as shown in FIG. 11F, strands 47' and 51' of suture 46' may be a different color or lighter shade as compared to strand 49'. The strands 47, 47', 49, 49', 51, 51' may be formed of a selected color along an entire length, so that when in a braiding pattern, a medical professional may be able to visualize a color contrast, or distinction, along the length of the braid in predetermined segment lengths. For example, a first strand 47, 47' may extend on an outer portion of the suture 46, 46' (e.g., braid) for a length L1, L1' every third portion, a second strand 49, 49' may extend on an outer portion of the suture 46, 46' for a length L2, L2' every third portion, and a third strand 51, 51' may extend on an outer portion of the suture 46, 46' for a length L3, L3' every third portion. For visual clarity, the strands are shown of like thickness, although it is understood that the strings, knots, sutures may be any thickness, and may be equal thicknesses, or different thicknesses. In other embodiments, the fibers within a given strand may have a color difference relative to the remainder of the strand.

An advantage of varying the appearance of strands along a length of the suture 46, 46' is that the appearance of the string or suture may vary along the length, providing feedback to the operator that the respective string or suture is moving and the balloon is everting. For example, a medical professional may be able to visualize movement of the suture by the color contrast of the suture 46, 46'. String or sutures may also be treated with surface modifications such as plasma, corona, or nanofiber surface application to modify surface properties thereof. Additionally, the braided string, knotted string, or sutures may also provide additional tensile strength for the balloon in that the string or sutures may act to absorb and dissipate forces acting on the balloon, thereby reducing the risk of the balloon detachment.

Additional feedback mechanisms may include filling the balloon 130 with agitated saline and visualizing air bubbles with ultrasound, and a sinusoidal pattern for the balloon, where the distances between maximums of a sinusoidal wave define an incremental distance of balloon eversion.

Figure 36A:
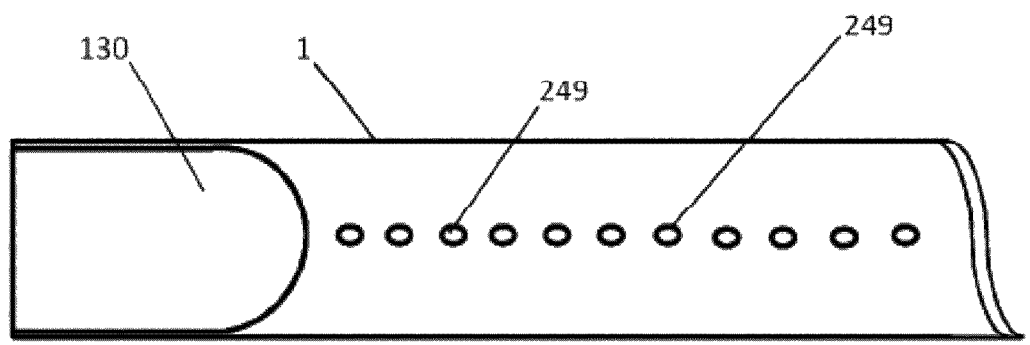
FIG. 36A illustrates a cross sectional view of an exemplary embodiment of a balloon in accordance with the present disclosure.
Figure 36B:
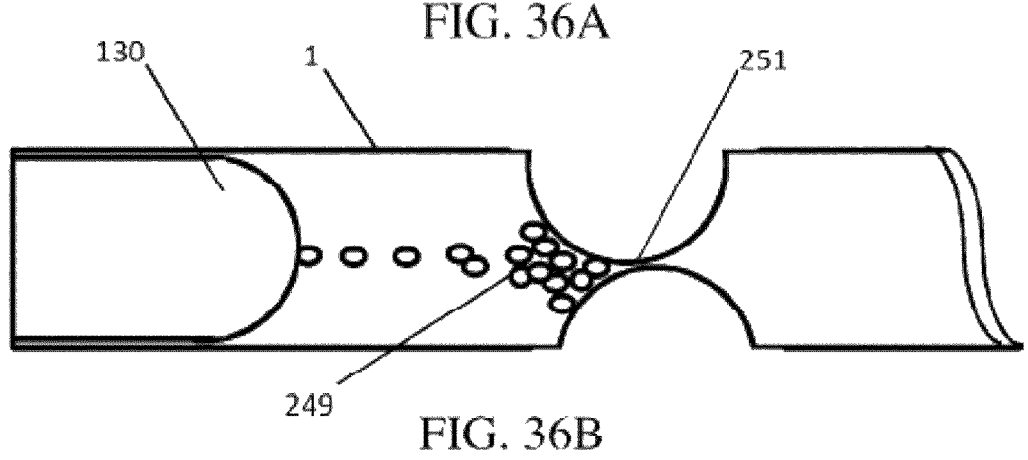
FIG. 36B illustrates a cross sectional view of an exemplary embodiment of a balloon in accordance with the present disclosure.

Navigation within the Fallopian tube and the indication of a clear path or obstructions may be provided by release of microbubbles from the tip of the balloon or from the distal end of the tube that the balloon everts from. Travel of the microbubbles may be trackable using imaging, such as ultrasound, to ascertain where a clear path exists. In instances of an obstruction 251, e.g., an occlusion or a constriction, the microbubbles may bunch up, or congregate, when the microbubbles are impeded. In response to detecting a grouping of microbubbles, a medical professional may be able to ascertain an obstruction. FIG. 36A illustrates a release of a stream of microbubbles 249 from a tip of the balloon 130 in the Fallopian tube 1 where no constrictions or obstructions are present, as evident by the steady continuous line of microbubbles 249. In some embodiments, microbubbles may be delivered through an inner lumen 54 of a balloon, as shown in FIGS. 17A-17B. The frequency or spacing of the microbubbles 249 may be controllable for finer measurements than with an air source that is modulated on or off, where the air is introduced to the fluid injected into the balloon 130. FIG. 36B illustrates a Fallopian tube 1 with a tubular constriction or obstruction 251, where the tubular constriction or obstruction 251 may impede a flow of microbubbles 249 and the microbubbles 249 begin to congregate, or bunch up, at the point of the constriction or obstruction 251. The bunching of the microbubbles 249 may provide a visual indication to the user where the constriction or obstruction 251 is in the Fallopian tube 1. In response to a detected obstruction 251, a medical professional may perform additional imaging, such as ultrasound, to determine where the balloon stopped.

The present disclosure further provides various methods for collecting cells from a lumen of a subject using embodiments of the catheter described above. Methods may include using a catheter including at least a tube, a balloon (with or without an extending portion) secured to a distal end of the tube, a push wire that actuates said balloon between an inverted position within the tube and an everted position extending beyond the distal end, and a slidable sheath coaxial with the tube, everting a first portion (approximately 1 to 2 cm according to some embodiments) of the balloon distally beyond the distal end of the tube to the preselected distance, positioning the sheath and everted first portion of the balloon proximate to the lumen of a subject, or combinations thereof.

The balloon may be inflated, or otherwise pressurized, for initial eversion of the balloon to occur. For example, by pressurizing the balloon, column strength may be provided to the balloon, allowing it to evert when a push wire is advanced. The sheath knob may be advanced to the first marker on the hypotube and/or catheter. The balloon may be everted to the point at the distal tip of the sheath. The distal tip of the sheath, and the pre-extended balloon, may be placed proximal to the ostium of the Fallopian tube. The sheath may be held in place by maintaining the sheath knob in a selected position, and the balloon and catheter may be further advanced, so that an initial portion of an everted balloon is inserted into the proximal os.

A medical professional may rotate a drive wheel for further eversion of the balloon and/or the suture as an extending portion. The drive wheel may be rotated until the balloon and/or suture is partially or fully everted. In some embodiments, a final everted length (e.g., approximately 7-12 cm) may be approximately equivalent to half of push wire travel. When the balloon and/or the suture is fully everted, the distal end of the push wire may remain in the catheter and may not contact the Fallopian tube.

The inflated balloon as fully everted in the Fallopian tube may fill the potential space of the Fallopian tube, contacting an inner surface of the Fallopian tube. The surface area contact may transfer cells onto the balloon surface. The balloon may be deflated while everted in the Fallopian tube, so that wrinkles in the balloon surface may capture cells collected on the balloon surface. In some embodiments, the balloon may be cycled between inflated and deflated while everted, for potentially increasing cell collection on the balloon surface and within the balloon surface features. In some embodiments, the suture may extend from the fully everted balloon, further collecting cells on the suture.

When cell collection on the balloon surface and/or the suture is complete, the medical professional may retract the handle of the device while holding the sheath in place, so that the everted balloon and/or the suture may be retracted within the sheath. A marker on the tube of the catheter when aligned with the sheath knob may provide an indication that the full length of the balloon/extending portion has been retracted with the sheath. The sheath may protect the collected cells on the balloon surface and/or the suture, for removing the device from the working channel of the hysteroscope.

By inserting the everted first portion of the balloon into the lumen, and further everting the balloon into the lumen using the push wire, cells may be collected on the balloon. Some embodiments of the method may also include adjusting a speed of the further everting step relative to the inserting the everted first portion of the balloon into the lumen step. A marker on the tube of the catheter when aligned with the sheath knob may provide an indication that the full length of the balloon/extending portion has been retracted with the sheath.

Any patents or publications mentioned in this specification are herein incorporated by reference to the same extent as if each individual publication was specifically and individually indicated to be incorporated by reference. The foregoing description is illustrative of particular embodiments of the disclosure, but is not meant to be a limitation upon the practice thereof.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It should be noted that the methods described herein do not have to be executed in the order described, or in any particular order. Moreover, various activities described with respect to the methods identified herein can be executed in serial or parallel fashion.

What is claimed is:

1. A device for Fallopian tube diagnostics, comprising:
   a tube having a distal end;
   a balloon having a first end coupled to the distal end of the tube, the balloon being disposed in the tube in a first, inverted position and movable to a second, everted position, extendable a distance distal of the distal end of the tube, such that a surface of the balloon is contactable with an inner surface of a Fallopian tube;
   wherein at least a majority of the length of the balloon is inelastic such that the balloon is configured to prevent over-expansion of the Fallopian tube during eversion;
   and a push wire having a distal end coupled to a second end of the balloon, wherein the balloon is movable from the first inverted position to the second everted position by actuation of the push wire;
   wherein the surface of the balloon includes a plurality of surface features for collection, retention, or both, of a tissue sample of the inner surface of the Fallopian tube.

2. The device according to claim 1, wherein the plurality of surface features comprise a plurality of wrinkles in the surface of the balloon, having at least one of a plurality of edges, micro-ridges, or overlapping material, or combinations thereof.

3. The device according to claim 1, wherein a plurality of wrinkles are formable in the balloon surface.

4. The device according to claim 1, wherein a plurality of wrinkles in the balloon surface are configured to retain at least a portion of the tissue sample after contacting the inner surface of the Fallopian tube.

5. The device according to claim 1, wherein the plurality of surface features are etched in the surface of the balloon.

6. The device according to claim 1, wherein a portion of the surface of the balloon is embossed to form a plurality of peaks and valleys.

7. The device according to claim 1, wherein the plurality of surface features improve adhesion of the tissue sample to the balloon surface compared to the balloon surface without the plurality of surface features.

8. The device according to claim 1, wherein the balloon is inflatable for moving the balloon from the first inverted position to the second everted position.

9. The device according to claim 1, further comprising a filament attached to the distal end of the push wire, wherein the filament is disposed within the balloon in the first inverted position, and the filament is extendable from the balloon in the second everted position.

10. A system for collecting a tissue sample in a body lumen, comprising:
- a tube having a distal end and a balloon having a first end coupled to the distal end of the tube and a second end coupled to a distal end of a push wire, the balloon being positionable in a first, inverted state;
- wherein the push wire is configured to advance to evert the balloon to a second, everted state, such that the balloon extends out of the distal end of the tube;
- wherein at least a majority of the length of the balloon is inelastic such that the balloon is configured to prevent over-expansion of the body lumen during eversion;
- wherein a surface of the balloon is configured in the second, everted state, to contact an inner surface of the body lumen for transference of the tissue sample to the balloon surface;
- and wherein the balloon surface includes a plurality of surface features for collection, retention, or both, of the tissue sample.

11. The system according to claim 10, wherein the plurality of surface features comprise a plurality of wrinkles in the surface of the balloon, having at least one of a plurality of edges, micro-ridges, or overlapping material, or combinations thereof.

12. The system according to claim 10, wherein a plurality of wrinkles are formable in the balloon surface.

13. The system according to claim 10, wherein a plurality of wrinkles in the balloon surface are configured to retain at least a portion of the tissue sample after contacting the inner surface of the body lumen.

14. The system according to claim 10, wherein the plurality of surface features are etched in the surface of the balloon.

15. The system according to claim 10, wherein the plurality of surface features improve adhesion of the tissue sample to the balloon surface compared to the balloon surface without the plurality of surface features.

16. A method for collecting a tissue sample in a body lumen, comprising:
- providing a tube having a distal end and a balloon having a first end coupled to the distal end of the tube and a second end coupled to a distal end of a push wire, the balloon being positioned in a first, inverted state;
- advancing the push wire to evert the balloon to a second, everted state, such that the balloon extends out of the distal end of the tube;
- wherein at least a majority of the length of the balloon is inelastic such that the balloon is configured to prevent over-expansion of the body lumen during eversion;
- contacting a balloon surface in the second, everted state, with an inner surface of the body lumen;
- and wherein the balloon surface includes a plurality of surface features for collection, retention, or both, of the tissue sample.

17. The method according to claim 16, wherein the plurality of surface features comprise a plurality of wrinkles in the surface of the balloon, having at least one of a plurality of edges, micro-ridges, or overlapping material, or combinations thereof.

18. The method according to claim 16, wherein a plurality of wrinkles are formable in the balloon surface.

19. The method according to claim 16, wherein a plurality of wrinkles in the balloon surface are configured to retain at least a portion of the tissue sample after contacting the inner surface of the body lumen.

20. The method according to claim 16, wherein the plurality of surface features improve adhesion of the tissue sample to the balloon surface compared to the balloon surface without the surface features.

* * * * *